United States Patent [19]

Torii et al.

[11] Patent Number: 4,784,734

[45] Date of Patent: Nov. 15, 1988

[54] AZETIDINONE DERIVATIVES AND PROCESS FOR THE PREPARATION OF THE SAME

[75] Inventors: Sigeru Torii; Kenji Uneyama; Hideo Tanaka; Junzo Nokami; Michio Sasaoka; Norio Saito; Takashi Shiroi, all of Okayama, Japan

[73] Assignee: Otsuka Kagaku Yakuhin Kabushiki Kaisha, Japan

[21] Appl. No.: 71,664

[22] Filed: Jul. 9, 1987

Related U.S. Application Data

[60] Division of Ser. No. 865,651, May 16, 1986, Pat. No. 4,689,411, which is a continuation of Ser. No. 524,689, Aug. 19, 1983, abandoned, which is a continuation-in-part of Ser. No. 364,405, Apr. 1, 1982, abandoned.

[51] Int. Cl.⁴ .............................................. C25B 3/06
[52] U.S. Cl. ..................... 204/81; 204/59 R; 204/72; 204/78; 540/358
[58] Field of Search ............... 204/81, 78, 72, 59 R; 540/358, 354

[56] References Cited

U.S. PATENT DOCUMENTS

| | | | |
|---|---|---|---|
| 4,525,304 | 6/1985 | Hall et al. | 204/78 |
| 4,532,077 | 7/1985 | Torii et al. | 204/81 |
| 4,599,151 | 7/1986 | Torii et al. | 204/81 |
| 4,603,014 | 7/1986 | Torii et al. | 204/81 |

Primary Examiner—John F. Niebling
Assistant Examiner—Steven P. Marquis
Attorney, Agent, or Firm—Larson and Taylor

[57] ABSTRACT

This invention provides azetidinone derivatives represented by the formula

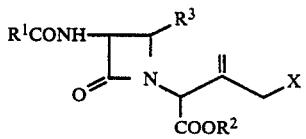

and processes for preparing the same. The azetidinone derivatives are used as the intermediates for producing cephalosporin compounds useful as antibiotic agents.

4 Claims, No Drawings

AZETIDINONE DERIVATIVES AND PROCESS FOR THE PREPARATION OF THE SAME

This is a division of application Ser. No. 865,651 filed May 16, 1986, now U.S. Pat. No. 4,689,411; which is a continuation of Ser. No. 524,689 filed Aug. 19, 1983, now abandoned; which is a continuation-in-part of Ser. No. 364,405 filed Apr. 1, 1982; now abandoned.

This invention relates to novel azetidinone derivatives and a process for preparing the same and more particularly to azetidinone derivatives represented by the formula

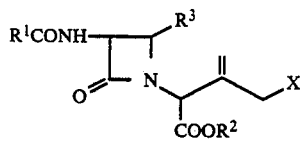 (I)

wherein $R^1$ is lower alkyl substituted with aryl or with aryloxy, $R^2$ is lower alkyl substituted with aryl or with aryloxy or lower alkyl optionally substituted with halogen, $R^3$ is

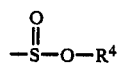

(wherein $R^4$ is lower alkyl),

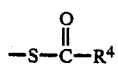

(wherein $R^4$ is as defined above),

(wherein $R^5$ is aryl,

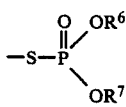

(wherein $R^6$ and $R^7$ are the same or different and lower alkyl or phenyl) or

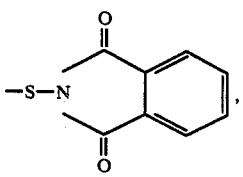

and X is hydrogen or halogen. The aryl and aryloxy groups stated above may have substituents.

The present invention provides novel intermediates for the preparation of cephalosporine compounds represented by the formula (IV) (to be hereinafter shown) which are useful as antibiotics.

The invention provides also processes for preparing the novel intermediates.

The invention further provides a novel process for preparing cephalosporine compounds represented by the formula (IV) from the foregoing intermediates.

Other features of the invention will be made apparent by the following description.

Examples of the aryl-substituted lower alkyl groups represented by $R^1$ in the formula (I) are benzyl, 2-phenylethyl, 3-phenylpropyl, 4-phenylbutyl, p-hydroxybenzyl, p-nitrobenzyl, p-chlorobenzyl, p-methoxybenzyl, 2-(p-chlorophenyl)ethyl, 3-(p-methoxybenzyl)propyl, etc. Examples of the aryloxy-substituted lower alkyl groups represented by $R^1$ are phenoxymethyl, 2-phenoxyethyl, 3-phenoxypropyl, 4-phenoxybutyl, p-hydroxyphenoxymethyl, p-nitrophenoxymethyl, p-methoxyphenoxymethyl, 2-(p-methoxyphenoxy)ethyl, 3-(p-nitrophenoxy)propyl and the like.

Examples of the lower alkyl groups represented by $R^2$ and substituted with aryl are benzyl, p-methoxybenzyl, p-chlorobenzyl, p-nitrobenzyl, diphenylmethyl, 2-phenylethyl, 3-phenylpropyl, 4-phenylbutyl, 2-(p-nitrophenyl)ethyl, 3-phenylpropyl, 3-(p-nitrophenyl)propyl, etc. Examples of the lower alkyl groups represented by $R^2$ and substituted with aryloxy are phenoxymethyl, p-nitrophenoxymethyl, 2-phenoxyethyl, 3-phenoxypropyl, 4-phenoxybutyl, 2-(p-nitrophenoxy)ethyl, 3-phenoxypropyl, 3-(p-nitrophenoxy)propyl, etc. Examples of the lower alkyl groups represented by $R^2$ and optionally substituted with halogen are methyl, ethyl, n-propyl, isopropyl, n-butyl, tert-butyl, 2-chloroethyl, 2,2,2-trichloroethyl, etc.

Examples of the lower alkyl groups represented by $R^4$, $R^6$ and $R^7$ are methyl, ethyl, n-propyl, isopropyl, n-butyl, tert-butyl, n-pentyl, n-hexyl, etc.

Exemplary of the aryl groups represented by $R^5$ are phenyl, p-chlorophenyl, p-methoxyphenyl, p-nitrophenyl, p-hydroxyphenyl, etc.

Halogen atoms represented by X include chlorine, bromine, iodine, etc.

Among the azetidinone derivatives of the formula (I), preferred are those having the formula

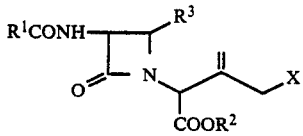 (I')

wherein $R^1$, $R^2$, $R^3$ and X are as defined above, but when X is hydrogen, $R^3$ is

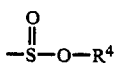

wherein $R^4$ is as defined above or

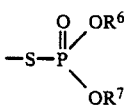

wherein $R^6$ and $R^7$ are as defined above.

The azetidinone derivatives of the formula (I) are divided into two classes of compounds represented by the formulae (Ia) and (Ib) respectively.

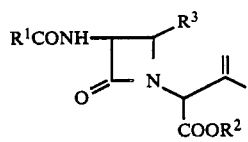

(Ia)

wherein $R^1$, $R^2$ and $R^3$ are as defined above.

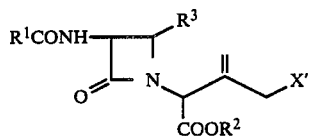

(Ib)

wherein $R^1$, $R^2$ and $R^3$ are as defined above and X' is halogen.

Preferred examples of the compounds having the formula (Ia) are the compounds represented by the formulae (Ic) and (Id) respectively.

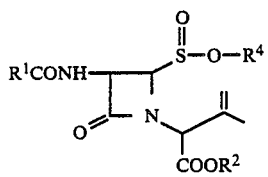

(Ic)

wherein $R^1$, $R^2$ and $R^4$ are as defined above.

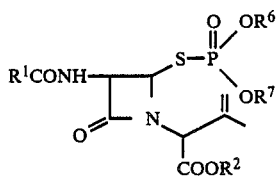

(Id)

wherein $R^1$, $R^2$, $R^6$ and $R^7$ are as defined above.

Specific examples of the compounds having the formula (Ic) are shown in Table I given below wherein $R^1$, $R^2$ and $R^4$ are specified.

TABLE I

| $R^1$ | $R^2$ | $R^4$ |
|---|---|---|
| ⟨C₆H₅⟩—CH₂— | CH₃— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| " | O₂N—⟨C₆H₄⟩—CH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |

TABLE I-continued

| $R^1$ | $R^2$ | $R^4$ |
|---|---|---|
| ⟨C₆H₅⟩—CH₂— | (C₆H₅)₂CH— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| " | Cl₃CCH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| ⟨C₆H₅⟩—CH₂— | (CH₃)₃C— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| " | ⟨C₆H₅⟩—CH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| ⟨C₆H₅⟩—CH₂— | CH₃O—⟨C₆H₄⟩—CH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| " | Cl—⟨C₆H₄⟩—CH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| CH₃O—⟨C₆H₄⟩—CH₂— | Cl—⟨C₆H₄⟩—CH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| " | ClCH₂CH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| Cl—⟨C₆H₄⟩—CH₂— | O₂N—⟨C₆H₄⟩—CH₂— | CH₃— |
| " | " | C₂H₅— |
| " | " | CH₃(CH₂)₂— |

TABLE I-continued

| R¹ | R² | R⁴ |
|---|---|---|
| " | " | (CH₃)₂CH— |
| " | " | CH₃(CH₂)₃— |
| " | " | (CH₃)₃C— |
| O₂N-C₆H₄-CH₂— | C₆H₅-O-CH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| C₆H₅-CH₂— | O₂N-C₆H₄-OCH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| C₆H₅-O-CH₂— | CH₃— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| C₆H₅-O-CH₂— | O₂N-C₆H₄-CH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| " | (C₆H₅)₂CH— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| CH₃O-C₆H₄-OCH₂— | (C₆H₅)₂CH— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| C₆H₅-O-CH₂— | Cl₃CCH₂— | CH₃— |
| " | " | C₂H₅— |
| " | " | CH₃(CH₂)₂— |
| " | " | (CH₃)₂CH— |
| " | " | CH₃(CH₂)₃— |

TABLE I-continued

| R¹ | R² | R⁴ |
|---|---|---|
| C₆H₅-O-CH₂— | (CH₃)₃C— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| " | C₆H₅-CH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| C₆H₅-O-CH₂— | CH₃O-C₆H₄-CH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| " | Cl-C₆H₄-CH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| O₂N-C₆H₄-OCH₂— | C₆H₅-OCH₂— | CH₃— |
| " | " | C₂H₅— |
| " | " | CH₃(CH₂)₂— |
| " | " | (CH₃)₂CH— |
| " | " | CH₃(CH₂)₃— |
| " | " | (CH₃)₃C— |
| C₆H₅-(CH₂)₂— | CH₃— | CH₃— |
| " | O₂N-C₆H₄-CH₂— | CH₃(CH₂)₂— |
| C₆H₅-(CH₂)₃— | (C₆H₅)₂CH— | (CH₃)₃C— |
| C₆H₅-(CH₂)₄— | ClCH₂CH₂— | C₂H₅— |
| Cl-C₆H₄-(CH₂)₂— | C₆H₅-OCH₂— | CH₃— |
| CH₃O-C₆H₄-(CH₂)₃— | Cl-C₆H₄-CH₂— | (CH₃)₃CH— |
| C₆H₅-O-(CH₂)₂— | ClCH₂CH₂— | CH₃(CH₂)₂— |

TABLE I-continued

| R¹ | R² | R⁴ |
|---|---|---|
| 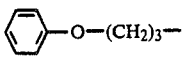 PhO—(CH₂)₃— | 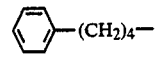 Ph—(CH₂)₄— | CH₃— |
| 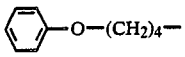 PhO—(CH₂)₄— | 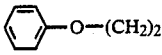 PhO—(CH₂)₂— | C₂H₅— |
| 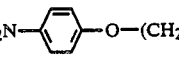 O₂N—C₆H₄—O—(CH₂)₃— | 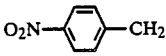 O₂N—C₆H₄—CH₂— | CH₃— |
| 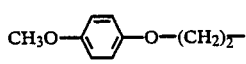 CH₃O—C₆H₄—O—(CH₂)₂— | Cl₃CCH₂— | C₂H₅— |

Specific examples of the compounds having the formula (Id) are shown in Table II given below wherein R¹, R², R⁶ and R⁷ are specified.

TABLE II

| R¹ | R² | R⁶ | R⁷ |
|---|---|---|---|
| 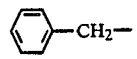 Ph—CH₂— | CH₃— | CH₃— | CH₃— |
| " | " | C₂H₅— | C₂H₅— |
| " | " |  4-CH₃-C₆H₄— |  4-C₂H₅-C₆H₄— |
| " | " | CH₃— |  C₆H₅— |
| " | " | C₂H₅— |  C₆H₅— |
| " | " | CH₃(CH₂)₂— | CH₃(CH₂)₂— |
| " | " | CH₃(CH₂)₃— | CH₃(CH₂)₃— |
| " | " | CH₃(CH₂)₂— |  C₆H₅— |
| " | " | CH₃(CH₂)₃— |  C₆H₅— |
| " | " | (CH₃)₂CH— | (CH₃)₂CH— |
| 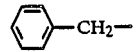 Ph—CH₂— | 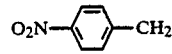 O₂N—C₆H₄—CH₂— | CH₃— | CH₃— |
| " | " | C₂H₅— | C₂H₅— |
| " | " |  4-CH₃-C₆H₄— |  4-C₂H₅-C₆H₄— |
| " | " | CH₃— |  C₆H₅— |
| " | " | C₂H₅— |  C₆H₅— |
| " | " | CH₃(CH₂)₂— | CH₃(CH₂)₂— |
| " | " | CH₃(CH₂)₃— | CH₃(CH₂)₃— |
| " | " | CH₃(CH₂)₂— |  C₆H₅— |
| " | " | CH₃(CH₂)₃— |  C₆H₅— |
| " | " | (CH₃)₂CH— | (CH₃)₂CH— |

-continued

| | | | |
|---|---|---|---|
| PhCH$_2$— | Ph$_2$CH— | CH$_3$— | CH$_3$— |
| " | " | C$_2$H$_5$— | C$_2$H$_5$— |
| " | " | C$_6$H$_4$CH$_3$— | C$_6$H$_4$C$_2$H$_5$— |
| " | " | CH$_3$— | C$_6$H$_5$— |
| " | " | C$_2$H$_5$— | C$_6$H$_5$— |
| " | " | CH$_3$(CH$_2$)$_2$— | CH$_3$(CH$_2$)$_2$— |
| " | " | CH$_3$(CH$_2$)$_3$— | CH$_3$(CH$_2$)$_3$— |
| " | " | CH$_3$(CH$_2$)$_2$— | C$_6$H$_5$— |
| " | " | CH$_3$(CH$_2$)$_3$— | C$_6$H$_5$— |
| " | " | (CH$_3$)$_2$CH— | (CH$_3$)$_2$CH— |
| PhCH$_2$— | Cl$_3$CCH$_2$— | CH$_3$— | CH$_3$— |
| " | " | C$_2$H$_5$— | C$_2$H$_5$— |
| " | " | C$_6$H$_4$CH$_3$— | C$_6$H$_4$C$_2$H$_5$— |
| " | " | CH$_3$— | C$_6$H$_5$— |
| " | " | C$_2$H$_5$— | C$_6$H$_5$— |
| " | " | CH$_3$(CH$_2$)$_2$— | CH$_3$(CH$_2$)$_2$— |
| " | " | CH$_3$(CH$_2$)$_3$— | CH$_3$(CH$_2$)$_3$— |
| " | " | CH$_3$(CH$_2$)$_2$— | C$_6$H$_5$— |
| " | " | CH$_3$(CH$_2$)$_3$— | C$_6$H$_5$— |
| " | " | (CH$_3$)$_2$CH— | (CH$_3$)$_2$CH— |
| PhCH$_2$— | (CH$_3$)$_3$C— | CH$_3$— | CH$_3$— |
| " | " | C$_2$H$_5$— | C$_2$H$_5$— |
| " | " | C$_6$H$_4$CH$_3$— | C$_6$H$_4$C$_2$H$_5$— |
| " | " | CH$_3$— | C$_6$H$_5$— |
| " | " | C$_2$H$_5$— | C$_6$H$_5$— |

-continued

| | | | |
|---|---|---|---|
| " | " | CH₃(CH₂)₂— | CH₃(CH₂)₂— |
| " | " | CH₃(CH₂)₃— | CH₃(CH₂)₃— |
| " | " | CH₃(CH₂)₂— | C₆H₅— |
| " | " | CH₃(CH₂)₃— | C₆H₅— |
| " | " | (CH₃)₂CH— | (CH₃)₂CH— |
| C₆H₅—CH₂— | C₆H₅—CH₂— | CH₃— | CH₃— |
| " | " | C₂H₅— | C₂H₅— |
| " | " | 3-CH₃-C₆H₄— | 3-C₂H₅-C₆H₄— |
| " | " | CH₃— | C₆H₅— |
| " | " | C₂H₅— | C₆H₅— |
| " | " | CH₃(CH₂)₂— | CH₃(CH₂)₂— |
| " | " | CH₃(CH₂)₃— | CH₃(CH₂)₃— |
| " | " | CH₃(CH₂)₂— | C₆H₅— |
| " | " | CH₃(CH₂)₃— | C₆H₅— |
| " | " | (CH₃)₂CH— | (CH₃)₂CH— |
| C₆H₅—CH₂— | 4-CH₃O-C₆H₄—CH₂— | CH₃— | CH₃— |
| " | " | C₂H₅— | C₂H₅— |
| " | " | 3-CH₃-C₆H₄— | 3-C₂H₅-C₆H₄— |
| " | " | CH₃— | C₆H₅— |
| " | " | C₂H₅— | C₆H₅— |
| " | " | CH₃(CH₂)₂— | CH₃(CH₂)₂— |
| " | " | CH₃(CH₂)₃— | CH₃(CH₂)₃— |
| " | " | CH₃(CH₂)₂— | C₆H₅— |
| " | " | CH₃(CH₂)₃— | C₆H₅— |
| " | " | (CH₃)₂CH— | (CH₃)₂CH— |
| C₆H₅—CH₂— | 4-Cl-C₆H₄—CH₂— | CH₃— | CH₃— |
| " | " | C₂H₅— | C₂H₅— |
| " | " | 3-CH₃-C₆H₄— | 3-C₂H₅-C₆H₄— |

-continued

| | | | |
|---|---|---|---|
| " | " | CH₃— | C₆H₅ |
| " | " | C₂H₅— | C₆H₅ |
| " | " | CH₃(CH₂)₂— | CH₃(CH₂)₂— |
| " | " | CH₃(CH₂)₃— | CH₃(CH₂)₃— |
| " | " | CH₃(CH₂)₂— | C₆H₅ |
| " | " | CH₃(CH₂)₃— | C₆H₅ |
| " | " | (CH₃)₂CH— | (CH₃)₂CH— |
| CH₃O—C₆H₄—CH₂— | Cl—C₆H₄—CH₂— | CH₃— | CH₃— |
| " | " | C₂H₅— | C₂H₅— |
| " | " | C₆H₄(CH₃)— | C₆H₄(C₂H₅)— |
| " | " | CH₃— | C₆H₅ |
| " | " | C₂H₅— | C₆H₅ |
| " | " | CH₃(CH₂)₂— | CH₃(CH₂)₂— |
| " | " | CH₃(CH₂)₃— | CH₃(CH₂)₃— |
| " | " | CH₃(CH₂)₂— | C₆H₅ |
| " | " | CH₃(CH₂)₃— | C₆H₅ |
| " | " | (CH₃)₂CH— | (CH₃)₂CH— |
| CH₃O—C₆H₄—CH₂— | ClCH₂CH₂— | CH₃— | CH₃— |
| " | " | C₂H₅— | C₂H₅— |
| " | " | C₆H₄(CH₃)— | C₆H₄(C₂H₅)— |
| " | " | CH₃— | C₆H₅ |
| " | " | C₂H₅— | C₆H₅ |
| " | " | CH₃(CH₂)₂— | CH₃(CH₂)₂— |
| " | " | CH₃(CH₂)₃— | CH₃(CH₂)₃— |
| " | " | CH₃(CH₂)₂— | C₆H₅ |
| " | " | CH₃(CH₂)₃— | C₆H₅ |
| " | " | (CH₃)₂CH— | (CH₃)₂CH— |

-continued

| | | | |
|---|---|---|---|
| 4-Cl-C₆H₄-CH₂- | 4-O₂N-C₆H₄-CH₂- | CH₃- | CH₃- |
| " | " | C₂H₅- | C₂H₅- |
| " | " | 2-CH₃-C₆H₄- | 2-C₂H₅-C₆H₄- |
| " | " | CH₃- | C₆H₅- |
| " | " | C₂H₅- | C₆H₅- |
| " | " | CH₃(CH₂)₂- | CH₃(CH₂)₂- |
| " | " | CH₃(CH₂)₃- | CH₃(CH₂)₃- |
| " | " | CH₃(CH₂)₂- | C₆H₅- |
| " | " | CH₃(CH₂)₃- | C₆H₅- |
| " | " | (CH₃)₂CH- | (CH₃)₂CH- |
| 4-O₂N-C₆H₄-CH₂- | C₆H₅-O-CH₂- | CH₃- | CH₃- |
| " | " | C₂H₅- | C₂H₅- |
| " | " | 2-CH₃-C₆H₄- | 2-C₂H₅-C₆H₄- |
| " | " | CH₃- | C₆H₅- |
| " | " | C₂H₅- | C₆H₅- |
| " | " | CH₃(CH₂)₂- | CH₃(CH₂)₂- |
| " | " | CH₃(CH₂)₃- | CH₃(CH₂)₃- |
| " | " | CH₃(CH₂)₂- | C₆H₅- |
| " | " | CH₃(CH₂)₃- | C₆H₅- |
| " | " | (CH₃)₂CH- | (CH₃)₂CH- |
| C₆H₅-CH₂- | 4-O₂N-C₆H₄-O-CH₂- | CH₃- | CH₃- |
| " | " | C₂H₅- | C₂H₅- |
| " | " | 2-CH₃-C₆H₄- | 2-C₂H₅-C₆H₄- |
| " | " | CH₃- | C₆H₅- |
| " | " | C₂H₅- | C₆H₅- |
| " | " | CH₃(CH₂)₂- | CH₃(CH₂)₂- |
| " | " | CH₃(CH₂)₃- | CH₃(CH₂)₃- |

-continued
| | | | |
|---|---|---|---|
| " | " | CH₃(CH₂)₂— |  |
| " | " | CH₃(CH₂)₃— |  |
| " | " | (CH₃)₂CH— | (CH₃)₂CH— |
| 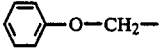 | CH₃— | CH₃— | CH₃— |
| " | " | C₂H₅— | C₂H₅— |
| " | " |  |  |
| " | " | CH₃— |  |
| " | " | C₂H₅— |  |
| " | " | CH₃(CH₂)₂— | CH₃(CH₂)₂— |
| " | " | CH₃(CH₂)₃— | CH₃(CH₂)₃— |
| " | " | CH₃(CH₂)₂— |  |
| " | " | CH₃(CH₂)₃— |  |
| " | " | (CH₃)₂CH— | (CH₃)₂CH— |
| 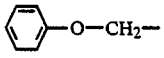 |  | CH₃— | CH₃— |
| " | " | C₂H₅— | C₂H₅— |
| " | " |  |  |
| " | " | CH₃— |  |
| " | " | C₂H₅— |  |
| " | " | CH₃(CH₂)₂— | CH₃(CH₂)₂— |
| " | " | CH₃(CH₂)₃— | CH₃(CH₂)₃— |
| " | " | CH₃(CH₂)₂— |  |
| " | " | CH₃(CH₂)₃— | 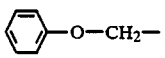 |
| " | " | (CH₃)₂CH— | (CH₃)₂CH— |
| 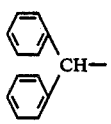 | | CH₃— | CH₃— |
| " | " | C₂H₅— | C₂H₅— |

-continued
| | | | |
|---|---|---|---|
| 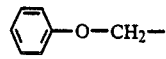 | 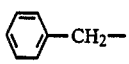 | CH₃(CH₂)₃— |  |
| " | " | (CH₃)₂CH—<br>CH₃— | (CH₃)₂CH—<br>CH₃— |
| " | " | C₂H₅— | C₂H₅— |
| " | " | 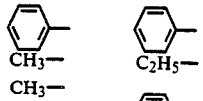 | 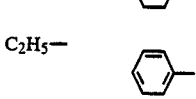 |
| " | " | C₂H₅— | 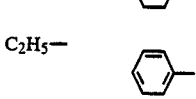 |
| "<br>" | "<br>" | CH₃(CH₂)₂—<br>CH₃(CH₂)₃— | CH₃(CH₂)₂—<br>CH₃(CH₂)₃— |
| " | " | CH₃(CH₂)₂— | 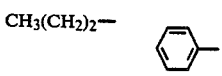 |
| " | " | CH₃(CH₂)₃— | 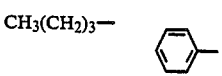 |
| " | " | (CH₃)₂CH—<br>CH₃— | (CH₃)₂CH—<br>CH₃— |
| 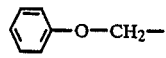 | 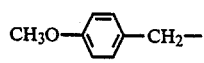 | | |
| " | " | C₂H₅— | C₂H₅— |
| " | " | 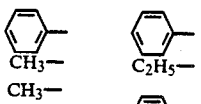 | 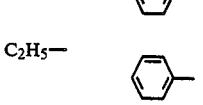 |
| " | " | C₂H₅— | 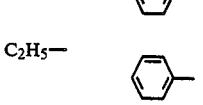 |
| "<br>" | "<br>" | CH₃(CH₂)₂—<br>CH₃(CH₂)₃— | CH₃(CH₂)₂—<br>CH₃(CH₂)₃— |
| " | " | CH₃(CH₂)₂— | 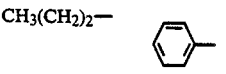 |
| " | " | CH₃(CH₂)₃— | 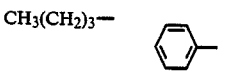 |
| " | " | (CH₃)₂CH—<br>CH₃— | (CH₃)₂CH—<br>CH₃— |
| 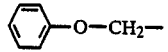 | 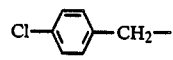 | | |
| " | " | C₂H₅— | C₂H₅— |
| " | " | 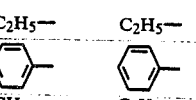 | 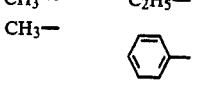 |
| " | " | C₂H₅— |  |

-continued

| | | | |
|---|---|---|---|
| " | " | CH₃(CH₂)₂— | CH₃(CH₂)₂— |
| " | " | CH₃(CH₂)₃— | CH₃(CH₂)₃— |
| " | " | CH₃(CH₂)₂— |  |
| " | " | CH₃(CH₂)₃— |  |
| " | " | (CH₃)₂CH— | (CH₃)₂CH— |
| O₂N—⌬—O—CH₂— | ⌬—O—CH₂— | CH₃— | CH₃— |
| " | " | C₂H₅— | C₂H₅— |
| " | " |  CH₃— |  C₂H₅— |
| " | " | CH₃— |  |
| " | " | C₂H₅— |  |
| " | " | CH₃(CH₂)₂— | CH₃(CH₂)₂— |
| " | " | CH₃(CH₂)₃— | CH₃(CH₂)₃— |
| " | " | CH₃(CH₂)₂— |  |
| " | " | CH₃(CH₂)₃— |  |
| " | " | (CH₃)₂CH— | (CH₃)₂CH— |
| CH₃O—⌬—O—CH₂— | CH— | CH₃— | CH₃— |
| " | " | C₂H₅— | C₂H₅— |
| " | " |  CH₃— |  C₂H₅— |
| " | " | CH₃— |  |
| " | " | C₂H₅— | 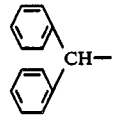 |
| " | " | CH₃(CH₂)₂— | CH₃(CH₂)₂— |
| " | " | CH₃(CH₂)₃— | CH₃(CH₂)₃— |
| " | " | CH₃(CH₂)₂— |  |
| " | " | CH₃(CH₂)₃— |  |
| " | " | (CH₃)₂CH— | (CH₃)₂CH— |
| (CH₂)₂— | CH₃— | CH₃— | CH₃— |

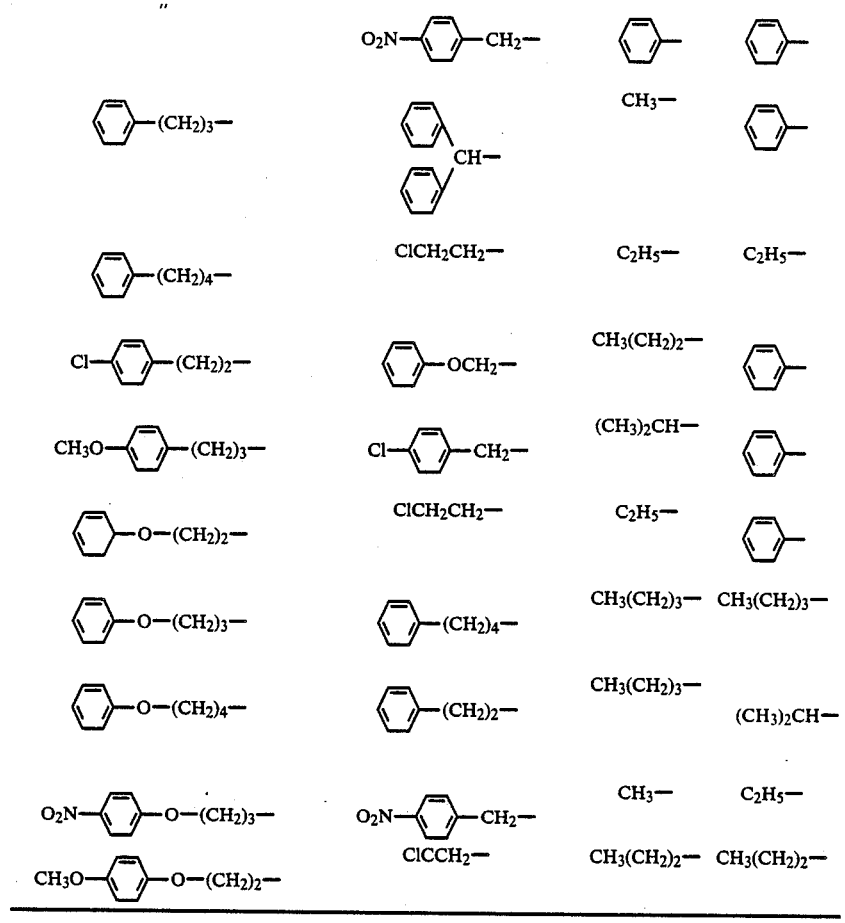
Specific examples of the compounds having the formula (Ib) are shown in Table III given below wherein $R^1$, $R^2$, $R^3$ and $X'$ are specified.
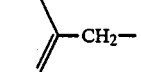

-continued
| | | | |
|---|---|---|---|
| " | " | 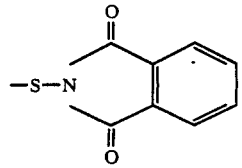 | " |
| " | 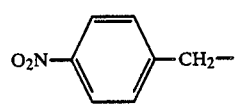 | 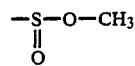 | " |
| " | " | 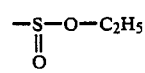 | " |
| " | " | 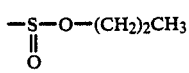 | " |
| " | " | 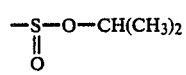 | " |
| " | " | 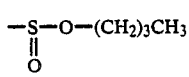 | " |
| " | " | 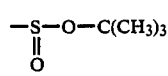 | " |
| " | " | 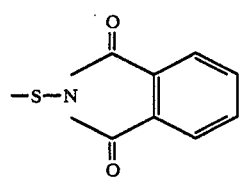 | " |
| " | 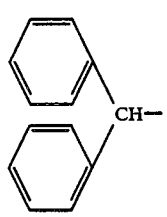 | 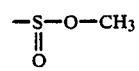 | " |
| " | " | 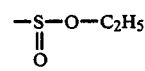 | " |
| " | " | 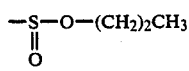 | " |
| " | " | 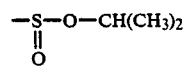 | " |
| " | " | 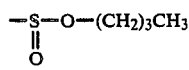 | " |
| " | " | 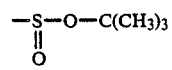 | " |

-continued

| | | | |
|---|---|---|---|
| " | " | —S—N(phthalimide) | " |
| " | Cl₃CCH₂— | —S(=O)—O—CH₃ | " |
| " | " | —S(=O)—O—C₂H₅ | " |
| " | " | —S(=O)—O—(CH₂)₂CH₃ | " |
| " | " | —S(=O)—O—CH(CH₃)₂ | " |
| " | " | —S(=O)—O—(CH₂)₃CH₃ | " |
| " | " | —S(=O)—O—C(CH₃)₃ | " |
| " | " | —S—N(phthalimide) | " |
| " | (CH₃)₃C— | —S(=O)—O—CH₃ | " |
| " | " | —S(=O)—O—C₂H₅ | " |
| " | " | —S(=O)—O—(CH₂)₂CH₃ | " |
| " | " | —S(=O)—O—CH(CH₃)₂ | " |
| " | " | —S(=O)—O—(CH₂)₃CH₃ | " |
| " | " | —S(=O)—O—C(CH₃)₃ | " |
| " | " | —S—N(phthalimide) | " |
| " | C₆H₅CH₂— | —S(=O)—O—CH₃ | " |

-continued

| | | | |
|---|---|---|---|
| " | " | −S(=O)−O−C₂H₅ | " |
| " | " | −S(=O)−O−(CH₂)₂CH₃ | " |
| " | " | −S(=O)−O−CH(CH₃)₂ | " |
| " | " | −S(=O)−O−(CH₂)₃CH₃ | " |
| " | " | −S(=O)−O−C(CH₃)₃ | " |
| " | " | −S−N(phthalimide) | " |
| " | 4-CH₃O-C₆H₄-CH₂− | −S(=O)−O−CH₃ | " |
| " | " | −S(=O)−O−C₂H₅ | " |
| " | " | −S(=O)−O−(CH₂)₂CH₃ | " |
| " | " | −S(=O)−O−CH(CH₃)₂ | " |
| " | " | −S(=O)−O−(CH₂)₃CH₃ | " |
| " | " | −S(=O)−O−C(CH₃)₃ | " |
| " | " | −S−N(phthalimide) | " |
| " | 4-Cl-C₆H₄-CH₂− | −S(=O)−O−CH₃ | " |
| " | " | −S(=O)−O−C₂H₅ | " |
| " | " | −S(=O)−O−(CH₂)₂CH₃ | " |
| " | " | −S(=O)−O−CH(CH₃)₂ | " |

-continued
| | | | |
|---|---|---|---|
| " | " | 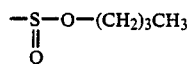 | " |
| " | " | 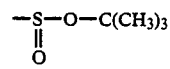 | " |
| " | " | 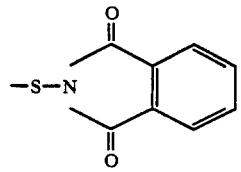 | " |
| 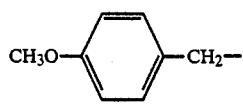 | " | 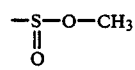 | " |
| " | " | 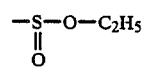 | " |
| " | " | 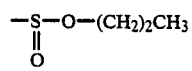 | " |
| " | " | 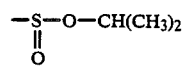 | " |
| " | " | 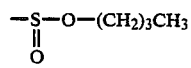 | " |
| " | " | 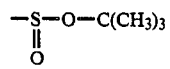 | " |
| " | " | 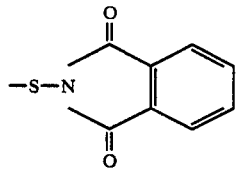 | " |
| " | 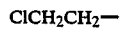 | 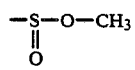 | " |
| " | " | 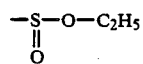 | " |
| " | " | 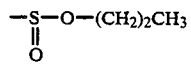 | " |
| " | " | 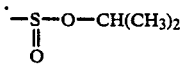 | " |
| " | " | 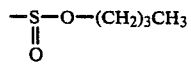 | " |
| " | " | 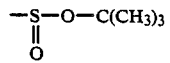 | " |

-continued

| | | | |
|---|---|---|---|
| " | " | —S—N(phthalimide) | " |
| 4-Cl-C6H4-CH2— | 4-O2N-C6H4-CH2— | —S(O)—O—CH3 | " |
| " | " | —S(O)—O—C2H5 | " |
| " | " | —S(O)—O—(CH2)2CH3 | " |
| " | " | —S(O)—O—CH(CH3)2 | " |
| " | " | —S(O)—O—(CH2)3CH3 | " |
| " | " | —S(O)—O—C(CH3)3 | " |
| " | " | —S—N(phthalimide) | " |
| 4-O2N-C6H4-CH2— | C6H5-O-CH2— | —S(O)—O—CH3 | " |
| " | " | —S(O)—O—C2H5 | " |
| " | " | —S(O)—O—(CH2)2CH3 | " |
| " | " | —S(O)—O—CH(CH3)2 | " |
| " | " | —S(O)—O—(CH2)3CH3 | " |
| " | " | —S(O)—O—C(CH3)3 | " |
| " | " | —S—N(phthalimide) | " |

-continued
| | | | |
|---|---|---|---|
| 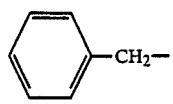 | 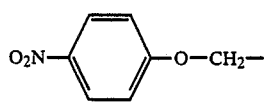 | 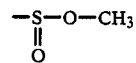 | " |
| " | " | 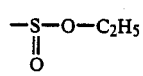 | " |
| " | " | 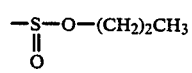 | " |
| " | " | 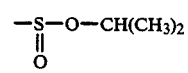 | " |
| " | " | 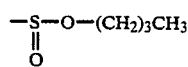 | " |
| " | " | 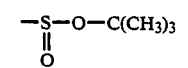 | " |
| " | " | 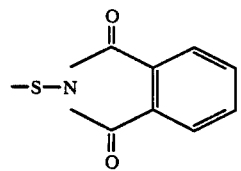 | " |
| 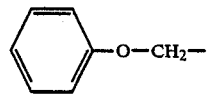 | CH$_3$— | 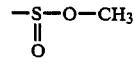 | " |
| " | " | 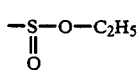 | " |
| " | " | 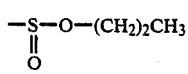 | " |
| " | " | 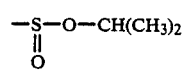 | " |
| " | " | 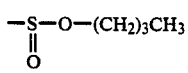 | " |
| " | " | 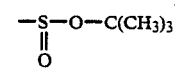 | " |
| " | " | 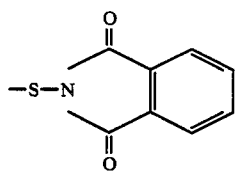 | " |
| " | 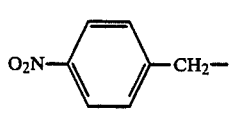 | 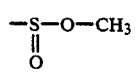 | " |
| " | " | 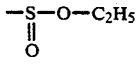 | " |

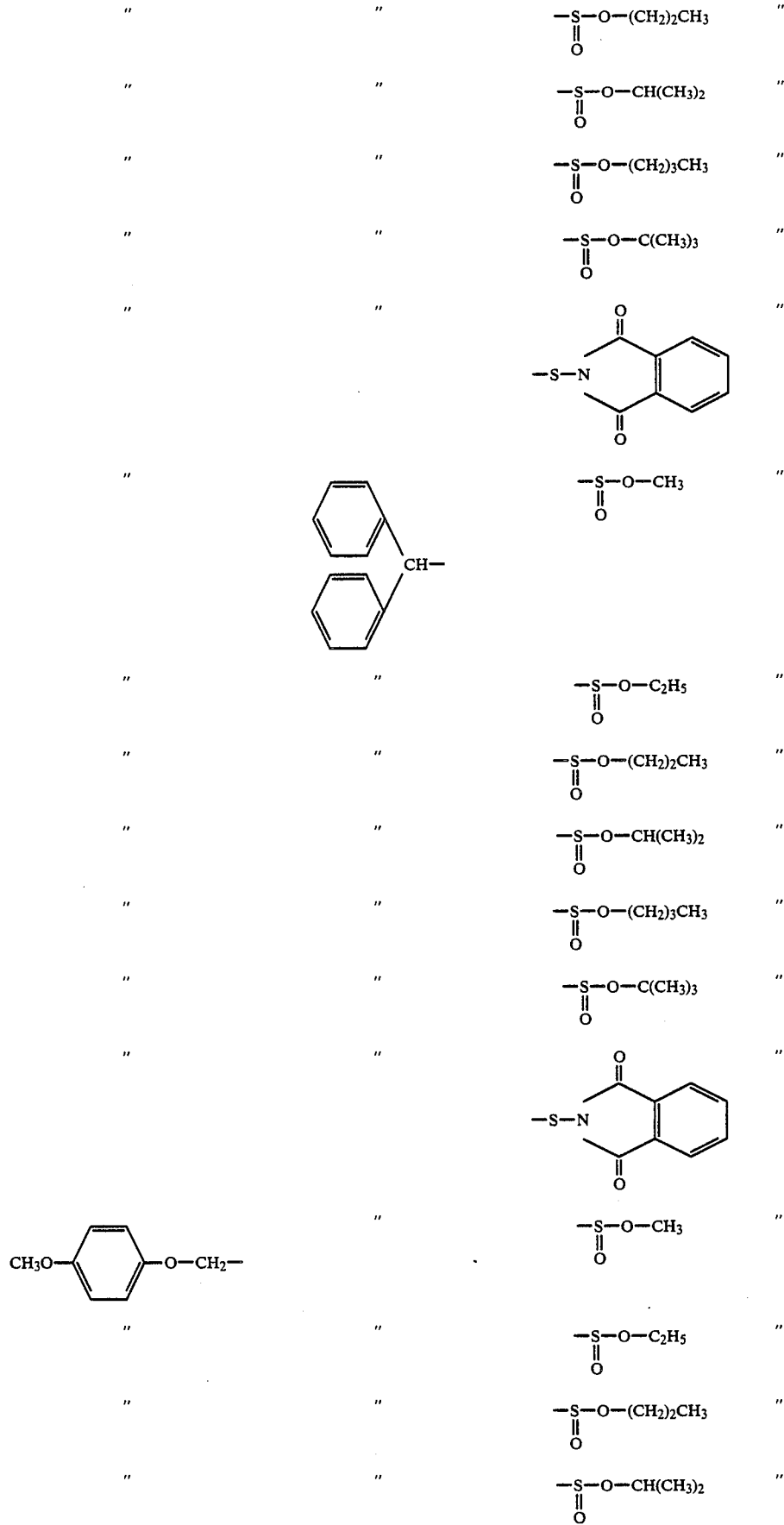

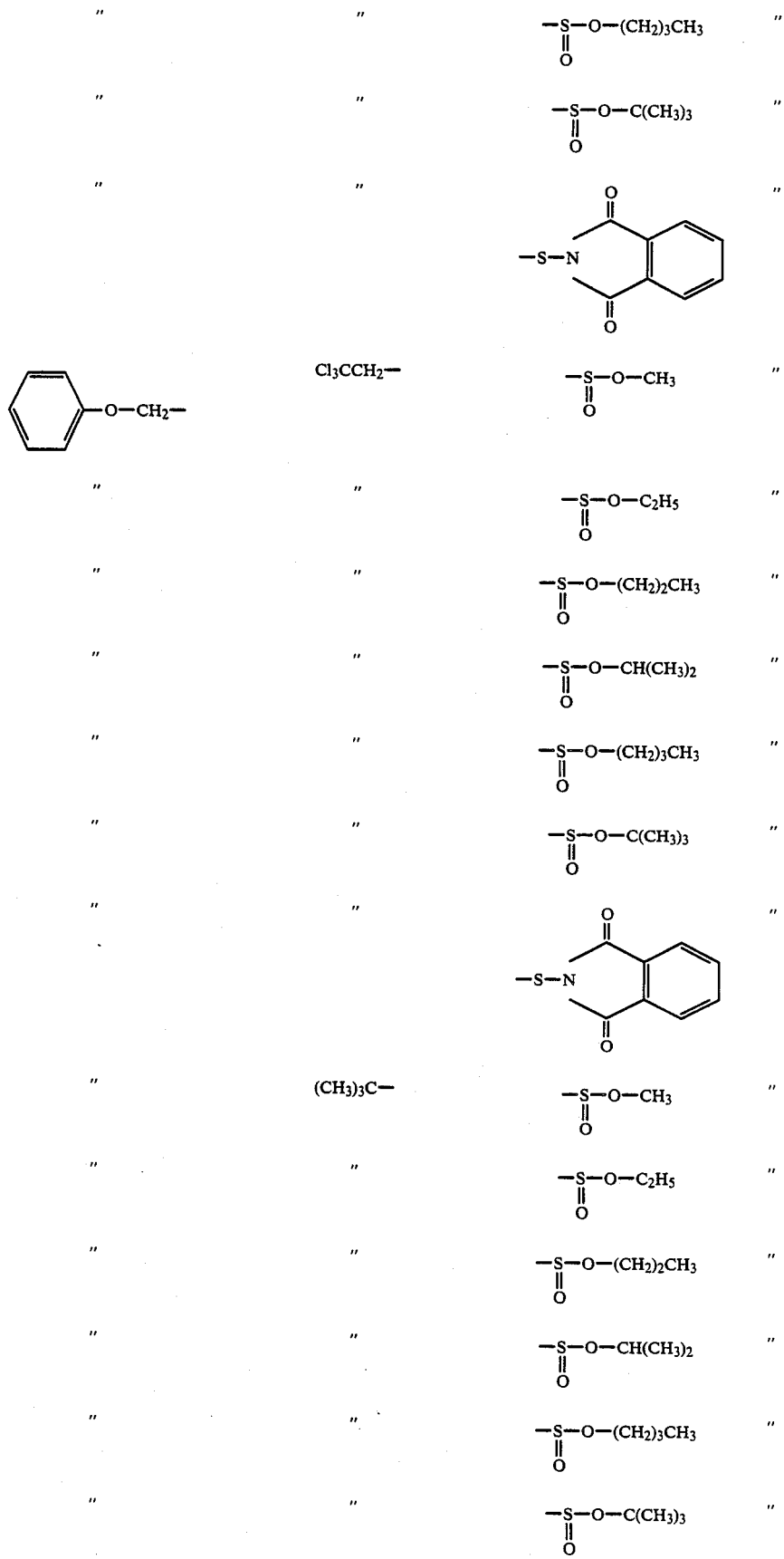

-continued
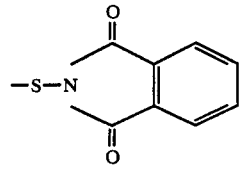
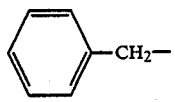
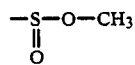
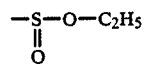
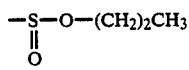
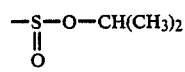
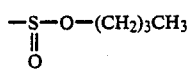
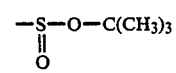
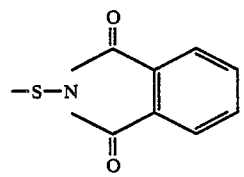
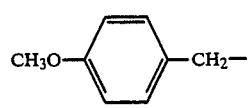
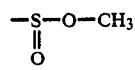
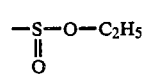
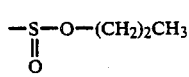
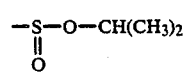
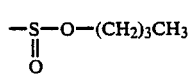
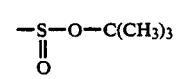
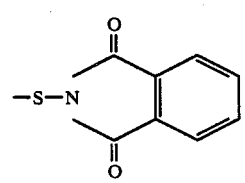

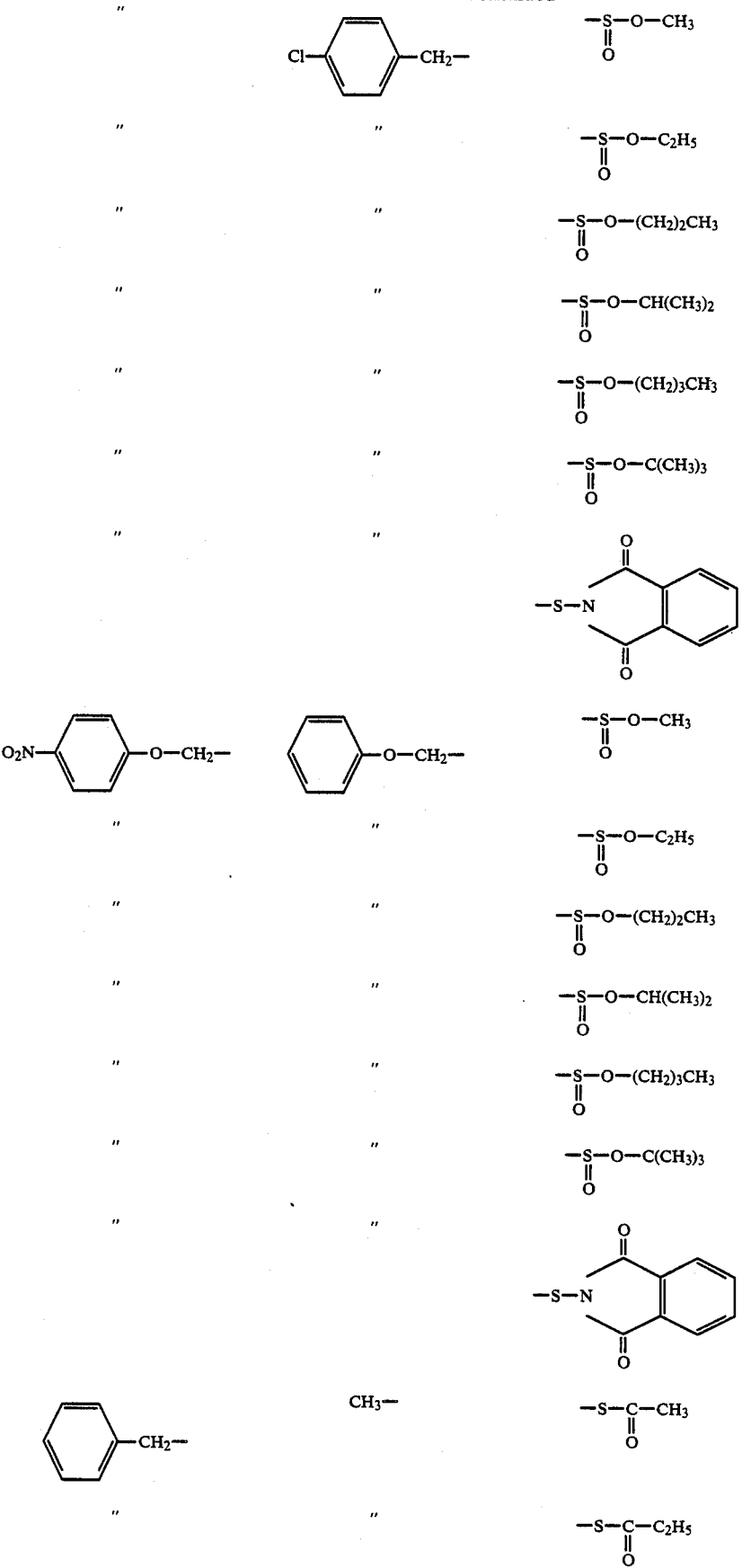

-continued
| | | | |
|---|---|---|---|
| " | " |  | " |
| " | " |  | " |
| " | " |  | " |
| " | " |  | " |
| " | " |  | " |
| " | " |  | " |
| " | " |  | " |
| " | " |  | " |
| " | " |  | " |
| " | 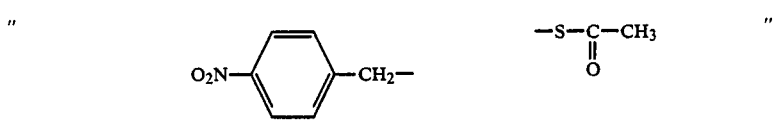 |  | " |
| " | " |  | " |
| " | " |  | " |
| " | " |  | " |
| " | " |  | " |
| " | " |  | " |

-continued
| " | " | 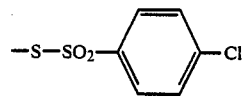 | " |
| " | " | 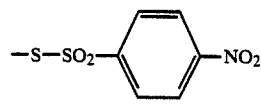 | " |
| " | " | 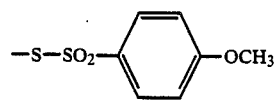 | " |
| " | " | 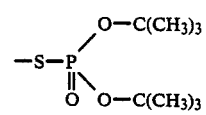 | " |
| " | 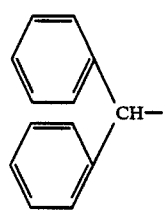 | 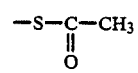 | " |
| " | " | 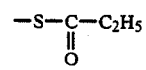 | " |
| " | " | 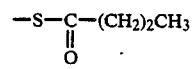 | " |
| " | " | 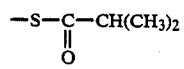 | " |
| " | " | 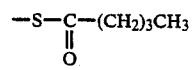 | " |
| " | " | 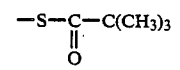 | " |
| " | " | 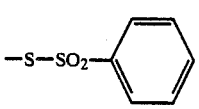 | " |
| " | " | 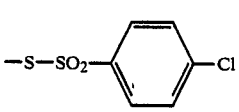 | " |
| " | " | 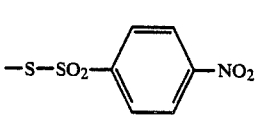 | " |
| " | " | 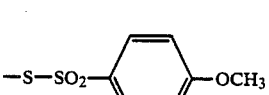 | " |

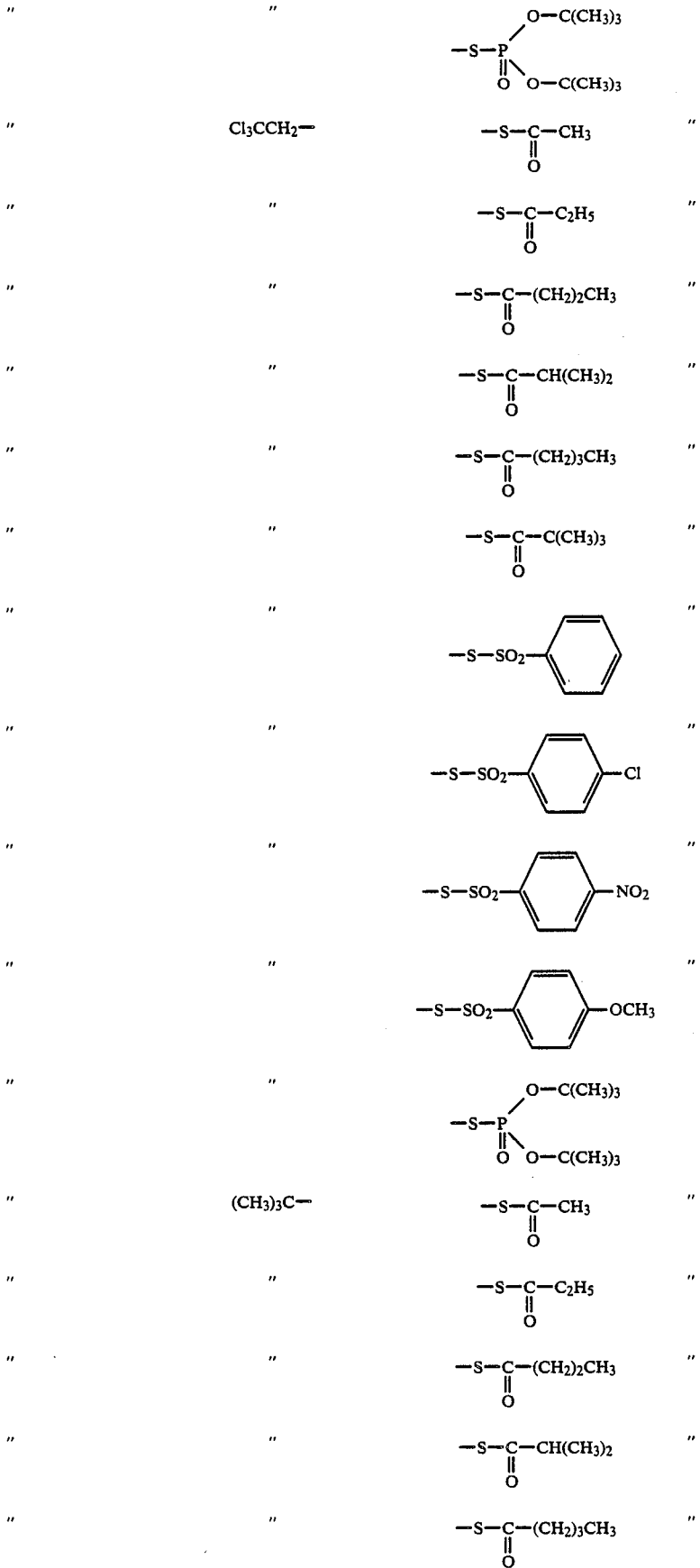

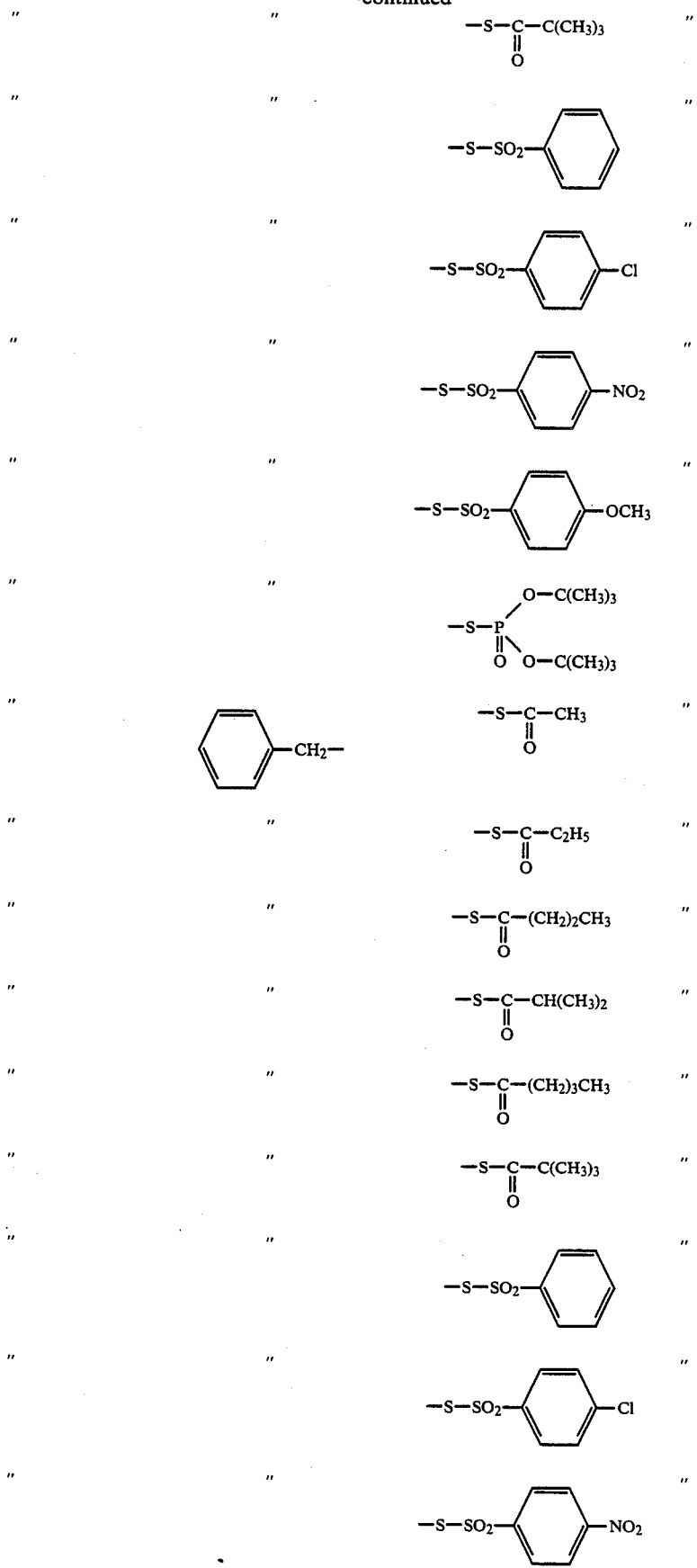

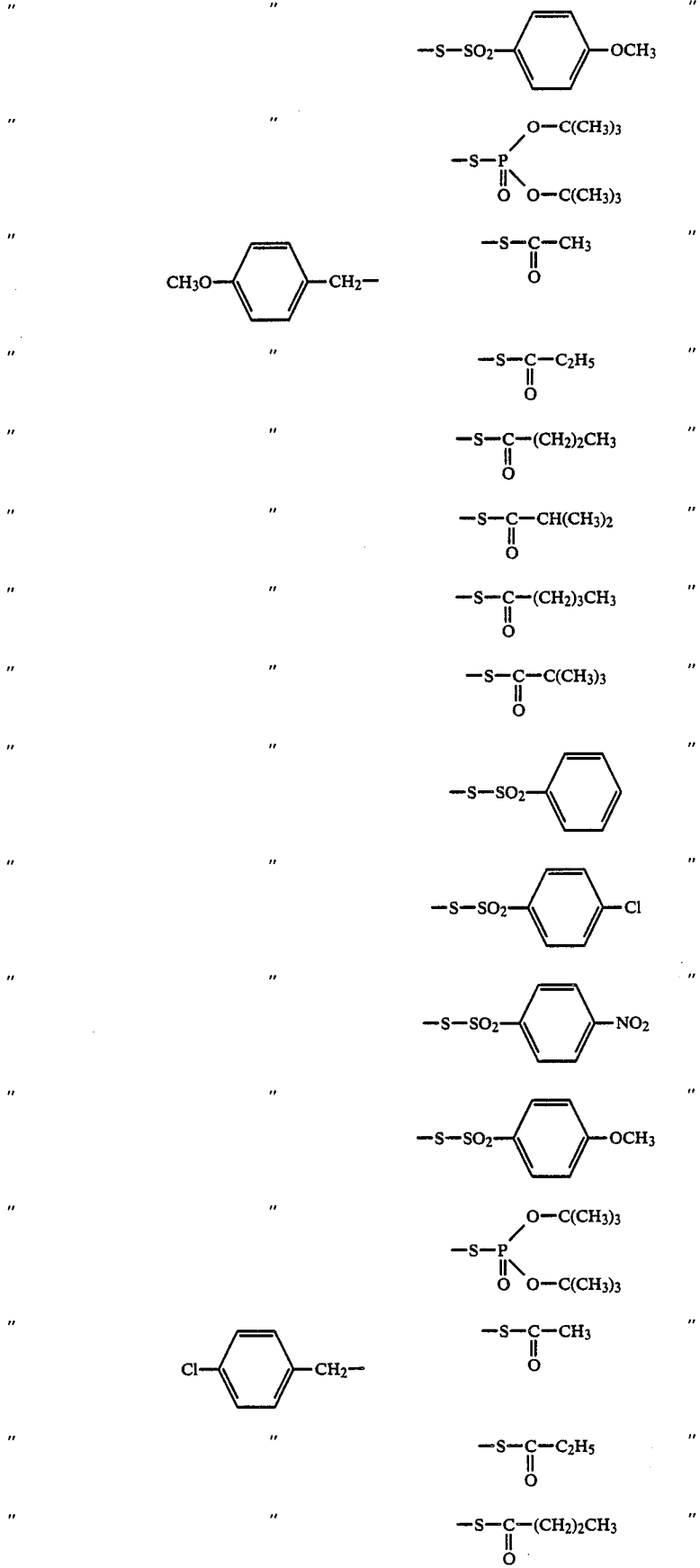

-continued
| | | | |
|---|---|---|---|
| " | " | 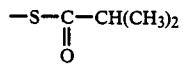 | " |
| " | " | 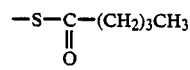 | " |
| " | " | 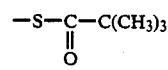 | " |
| " | " | 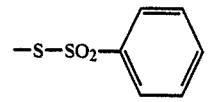 | " |
| " | " | 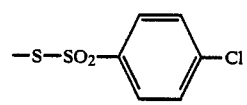 | " |
| " | " | 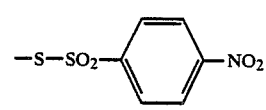 | " |
| " | " | 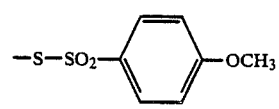 | " |
| " | " | 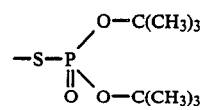 | " |
| 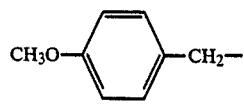 | 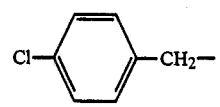 | 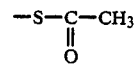 | " |
| " | " | 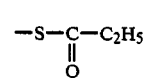 | " |
| " | " | 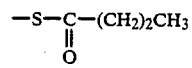 | " |
| " | " | 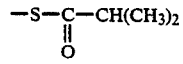 | " |
| " | " | 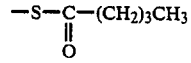 | " |
| " | " | 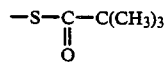 | " |
| " | " | 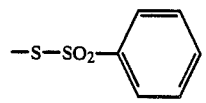 | " |
| " | " | 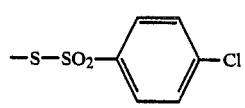 | " |

-continued
| | | | |
|---|---|---|---|
| " | " | 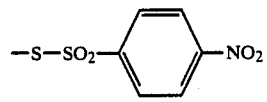 | " |
| " | " | 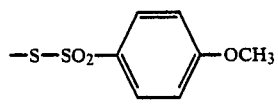 | " |
| " | " | 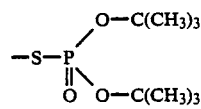 | " |
| " | ClCH$_2$CH$_2$— | 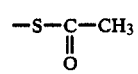 | " |
| " | " | 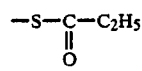 | " |
| " | " | 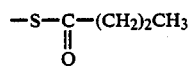 | " |
| " | " | 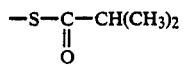 | " |
| " | " | 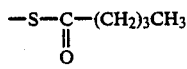 | " |
| " | " | 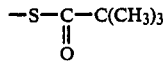 | " |
| " | " | 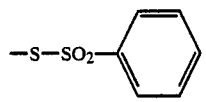 | " |
| " | " | 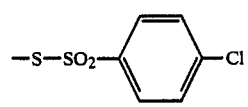 | " |
| " | " | 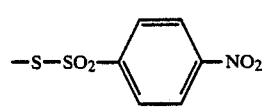 | " |
| " | " | 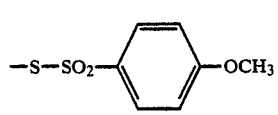 | " |
| " | " | 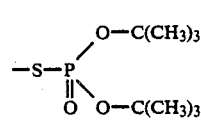 | " |
| 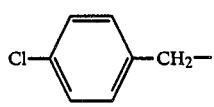 | 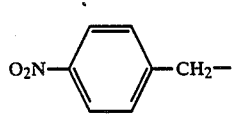 | 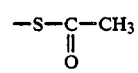 | " |

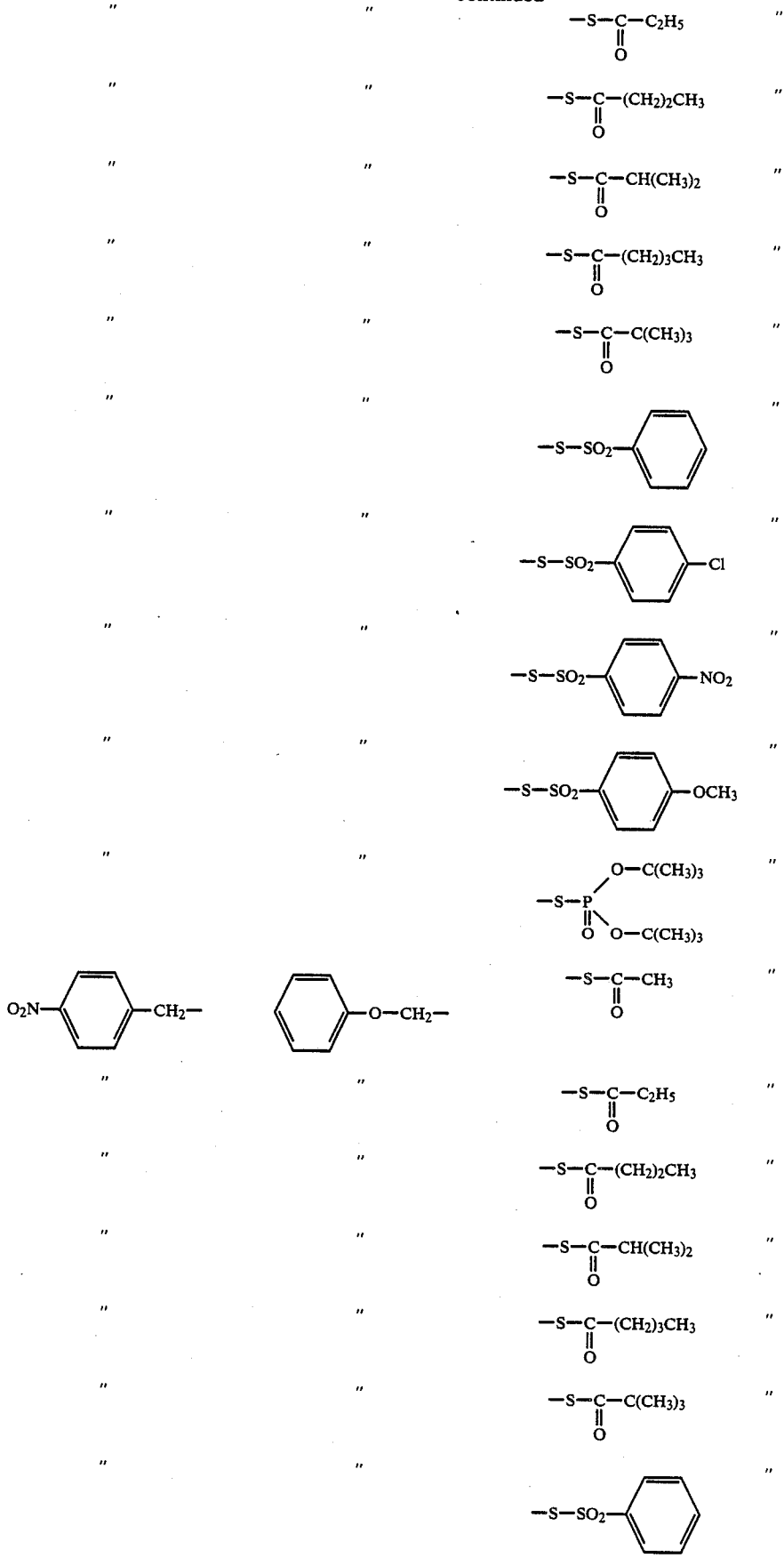

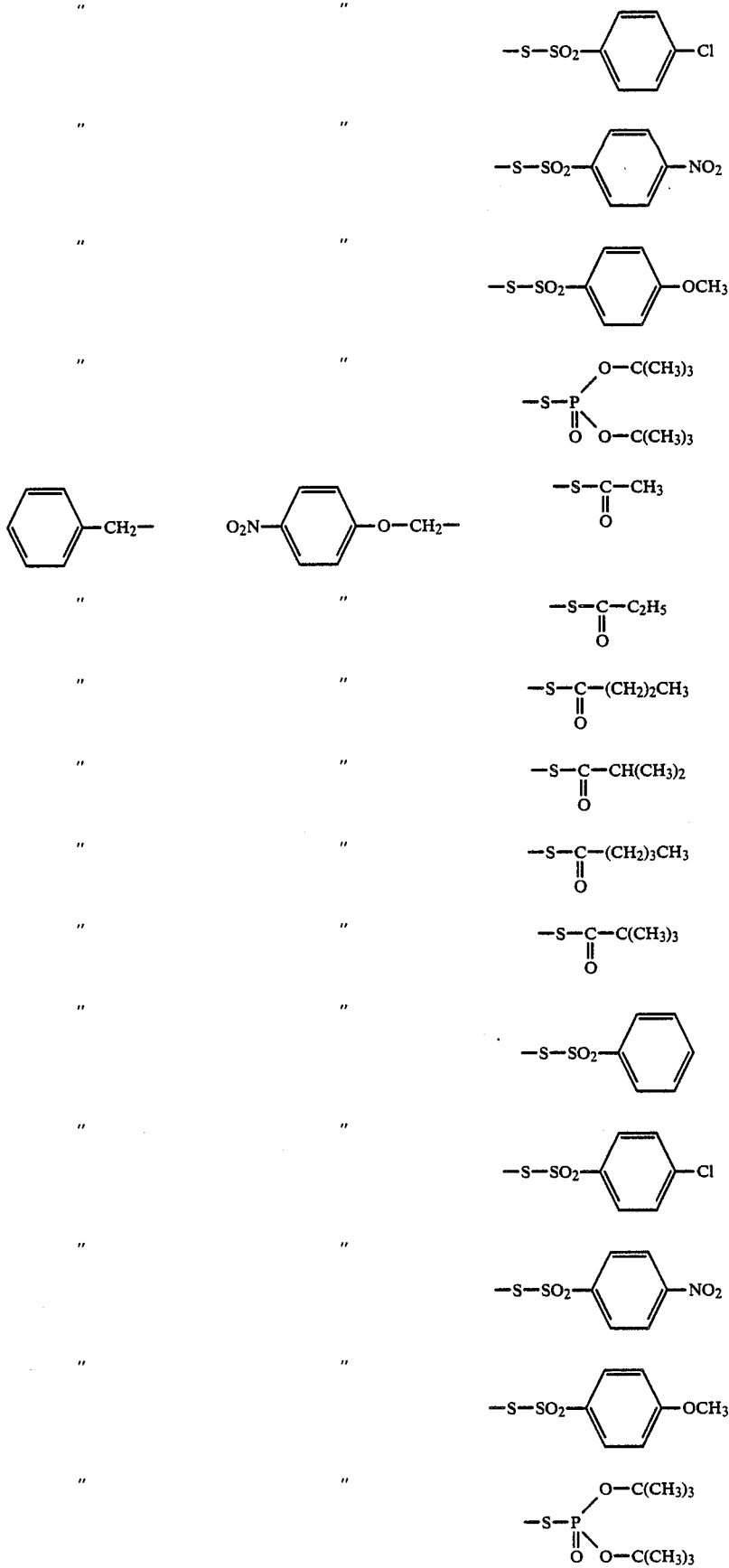

-continued
| | | | |
|---|---|---|---|
| 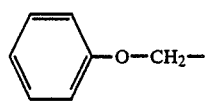 | CH$_3$— | 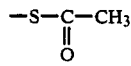 | " |
| " | " | 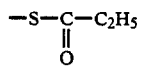 | " |
| " | " | 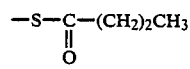 | " |
| " | " | 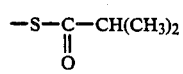 | " |
| " | " | 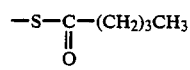 | " |
| " | " | 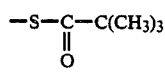 | " |
| " | " | 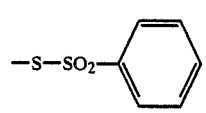 | " |
| " | " | 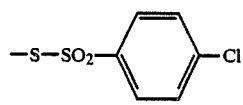 | " |
| " | " | 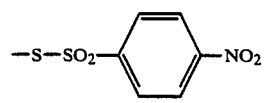 | " |
| " | " | 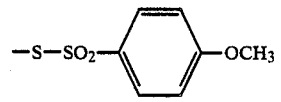 | " |
| " | " | 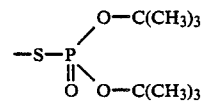 | " |
| " | 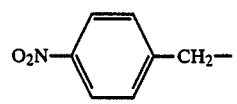 | 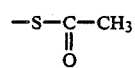 | " |
| " | " | 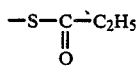 | " |
| " | " | 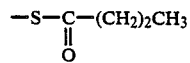 | " |
| " | " | 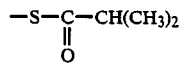 | " |
| " | " | 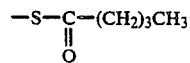 | " |
| " | " | 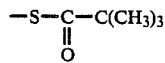 | " |

-continued
| | | |
|---|---|---|
| " | " | 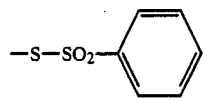 |
| " | " | 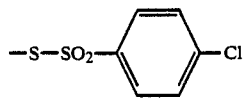 |
| " | " | 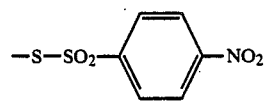 |
| " | " | 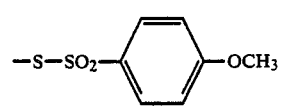 |
| " | " | 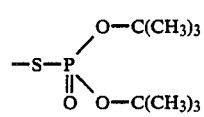 |
| " | 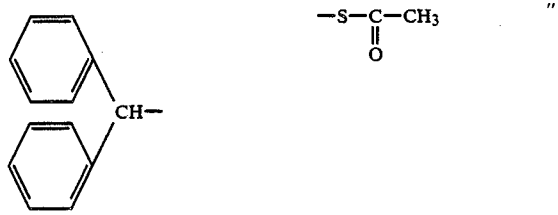 | 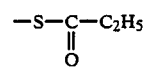 |
| " | " | 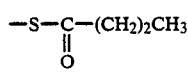 |
| " | " | 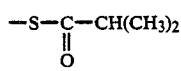 |
| " | " | 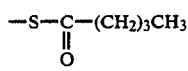 |
| " | " | 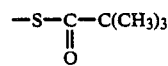 |
| " | " | 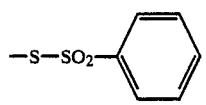 |
| " | " | 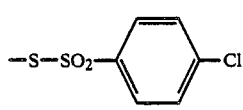 |
| " | " | 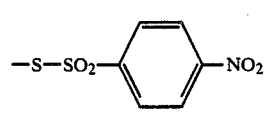 |

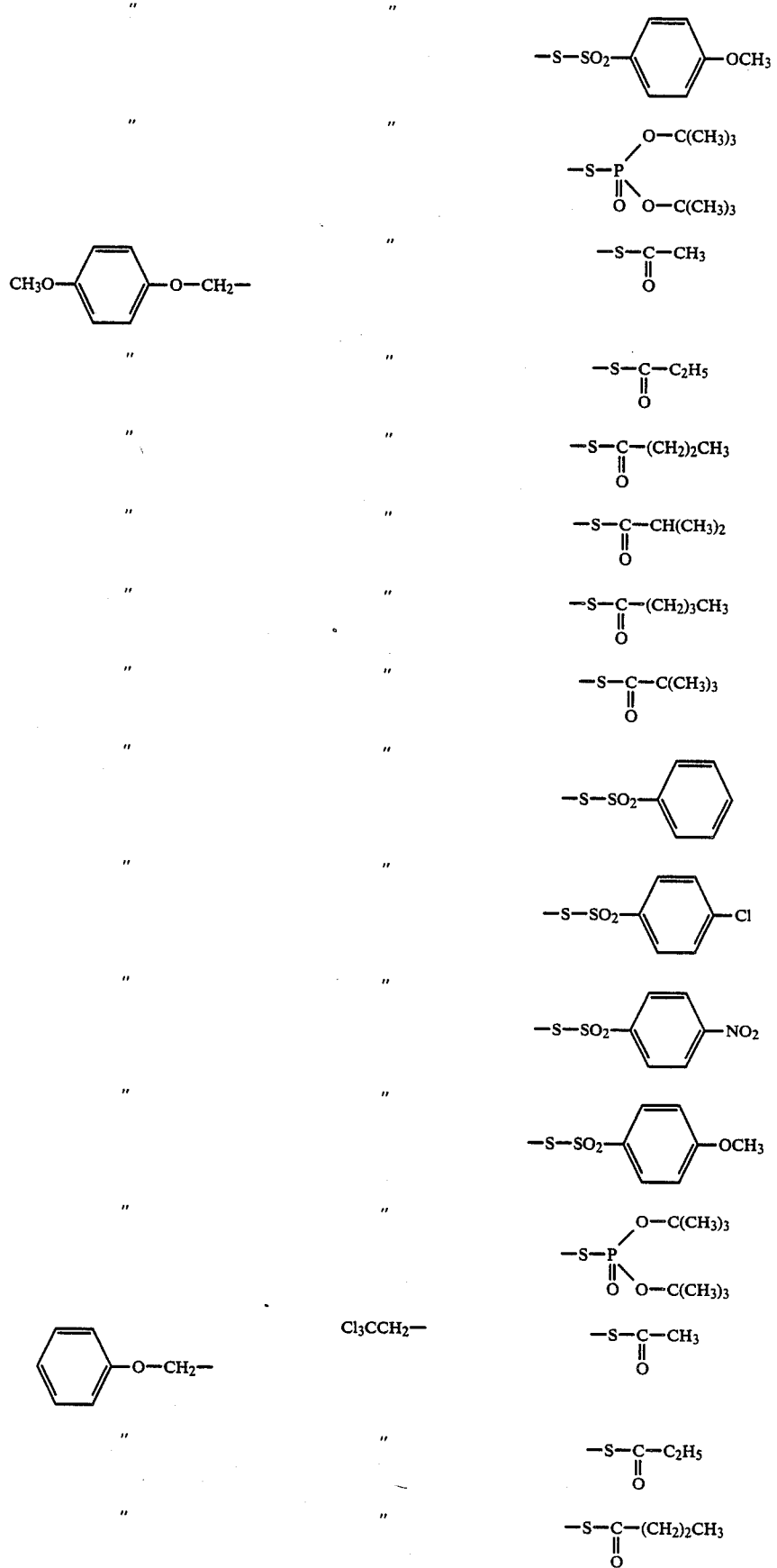

-continued
| | | | |
|---|---|---|---|
| " | " |  | " |
| " | " |  | " |
| " | " |  | " |
| " | " |  | " |
| " | " |  | " |
| " | " |  | " |
| " | " |  | " |
| " | " |  | " |
| " | (CH$_3$)$_3$C— |  | " |
| " | " |  | " |
| " | " |  | " |
| " | " |  | " |
| " | " |  | " |
| " | " |  | " |
| " | " |  | " |
| " | " |  | " |

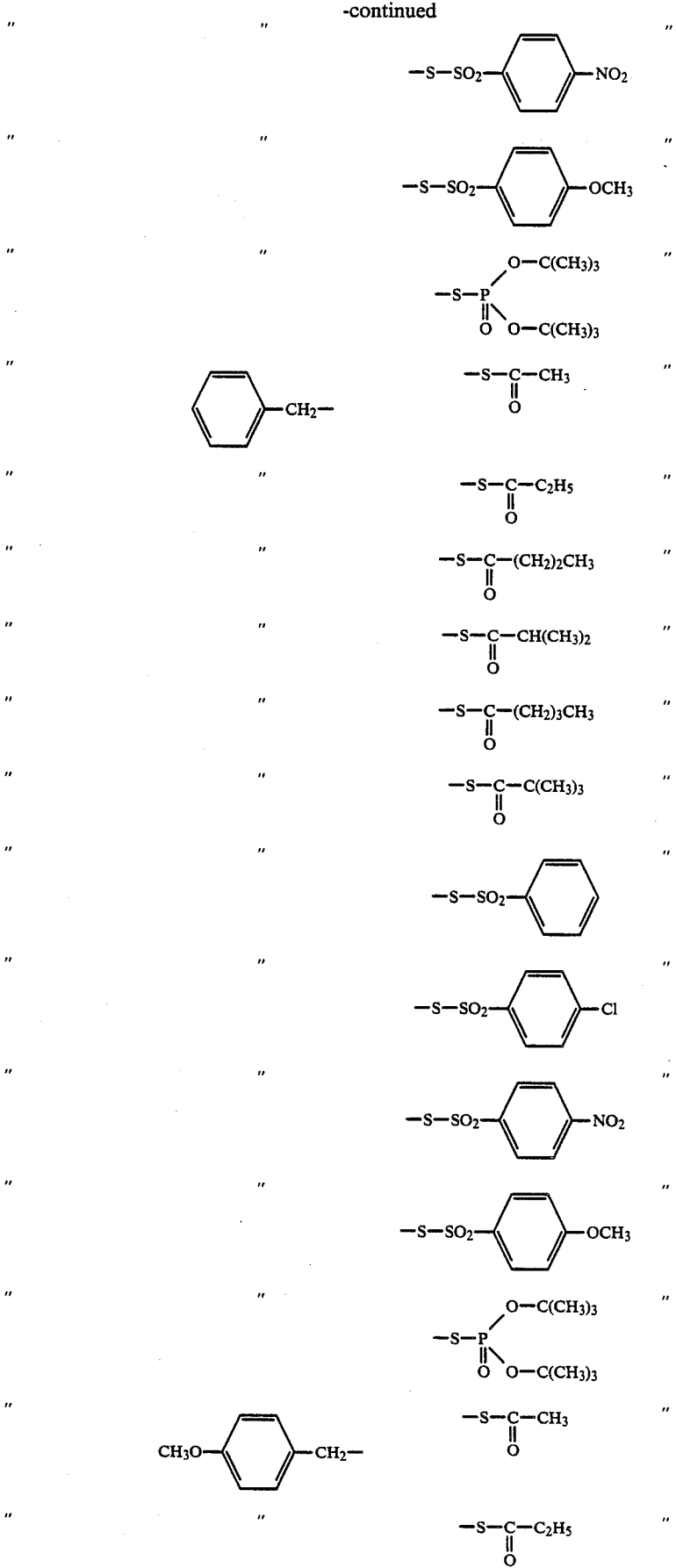

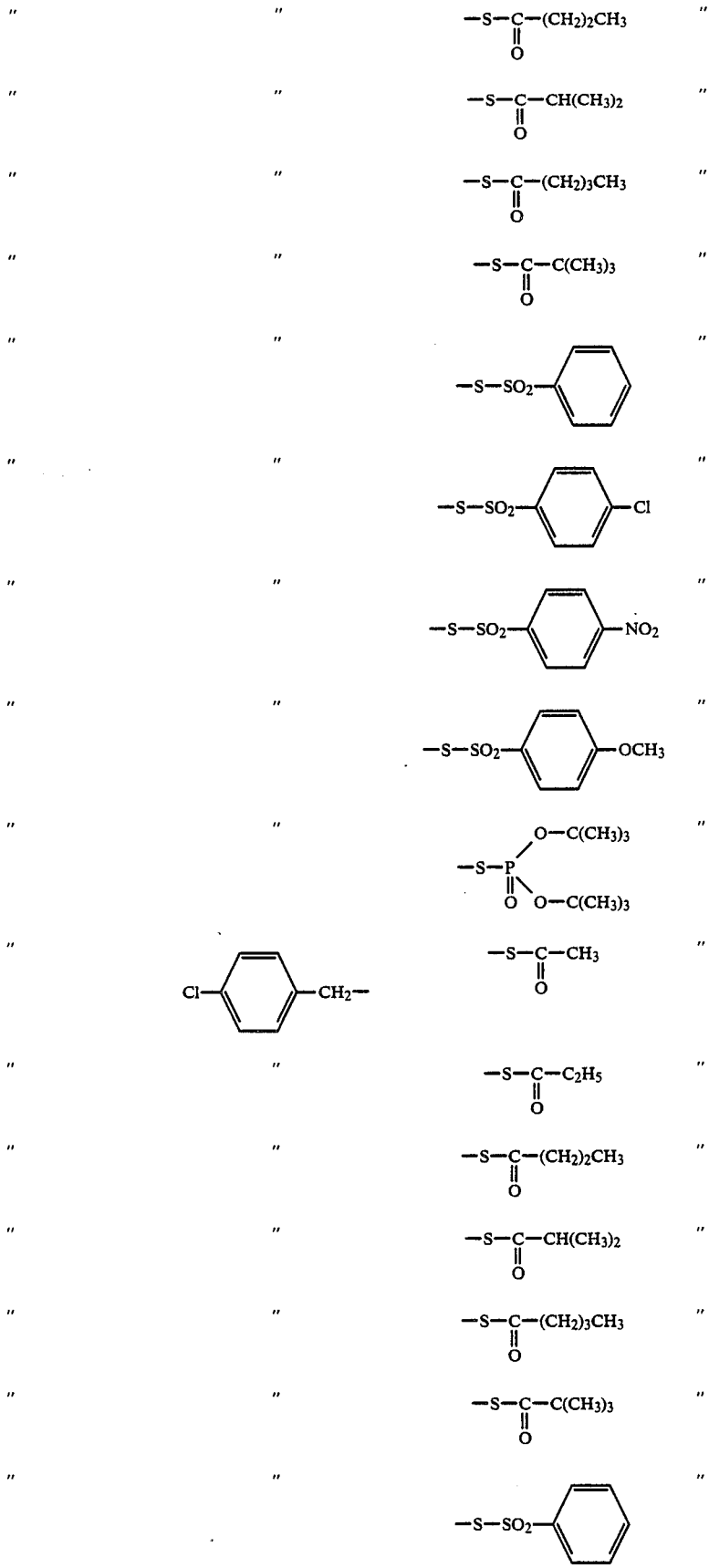

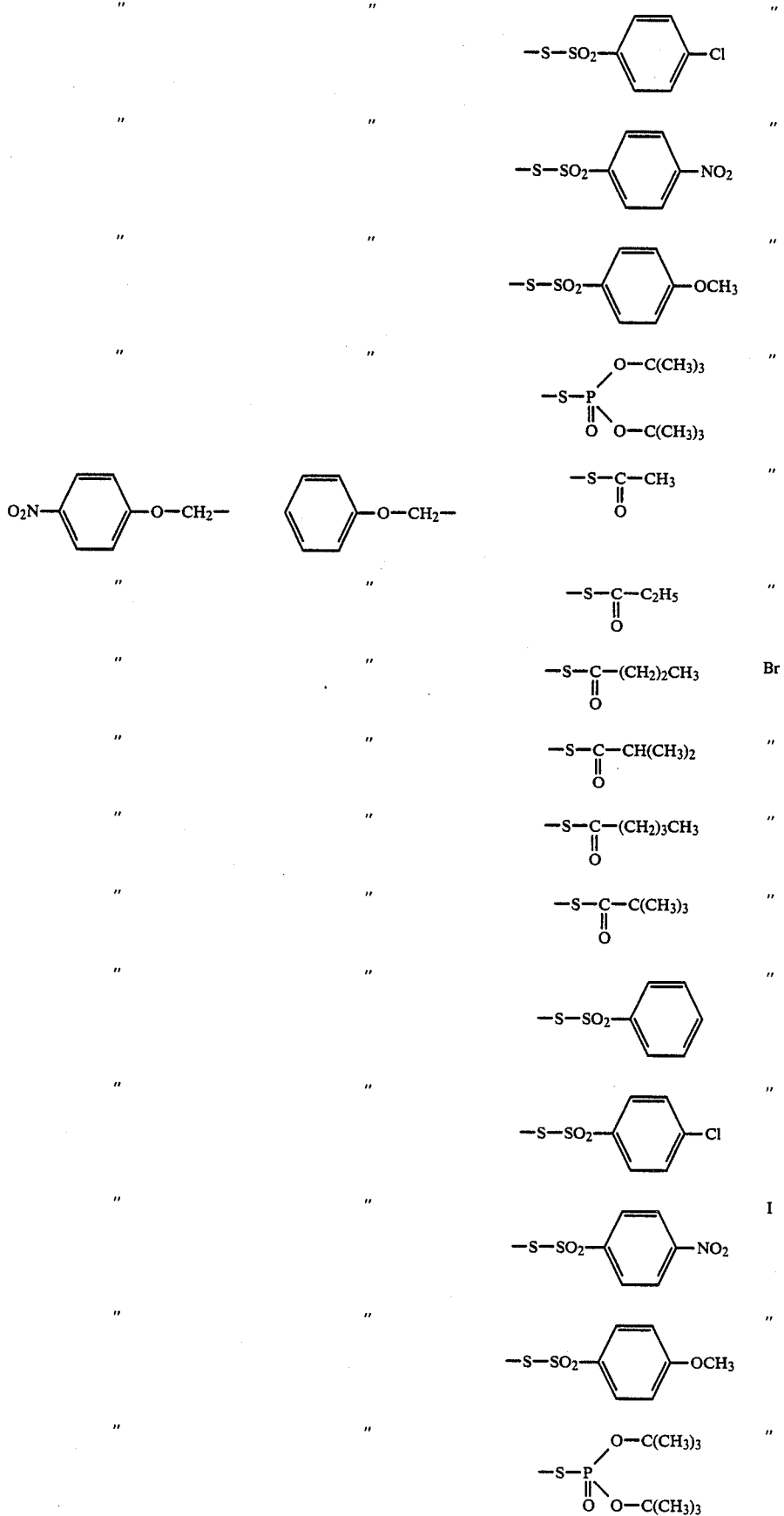

-continued
| | | | |
|---|---|---|---|
| 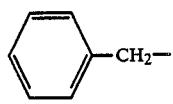 | CH₃— | 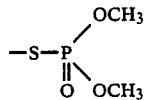 | Cl |
| " | " | 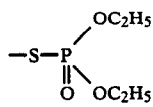 | " |
| " | " | 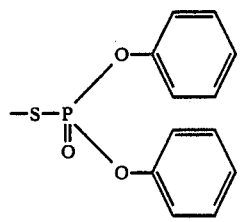 | " |
| " | " | 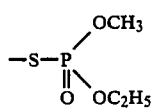 | " |
| " | " | 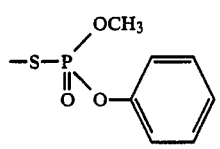 | " |
| " | " | 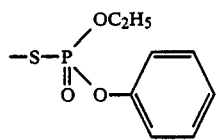 | " |
| " | " | 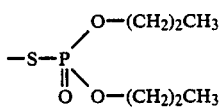 | " |
| " | " | 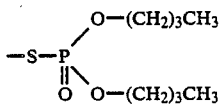 | " |
| " | " | 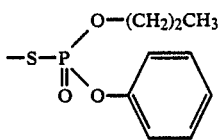 | " |
| " | " | 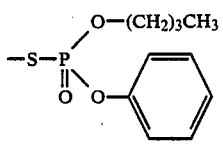 | " |
| " | " | 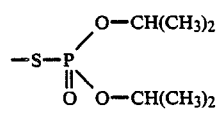 | " |
| " | 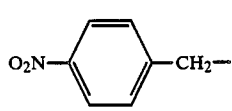 | 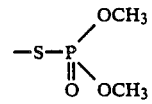 | " |

-continued
|  |  |  |  |
|--|--|--|--|
| " | " | 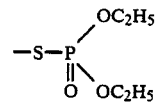 | " |
| " | " | 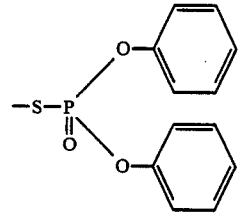 | " |
| " | " | 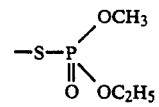 | " |
| " | " | 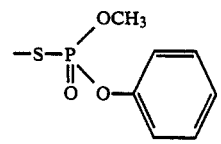 | " |
| " | " | 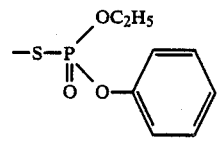 | " |
| " | " | 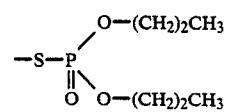 | " |
| " | " | 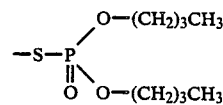 | " |
| " | " | 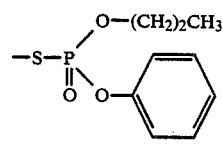 | " |
| " | " | 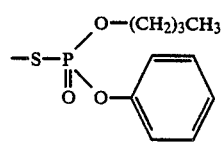 | " |
| " | " | 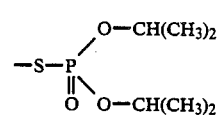 | " |
| " | 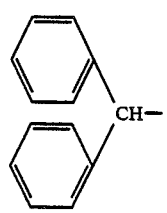 | 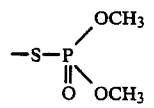 | " |

-continued
" " 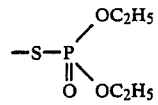 "
" " 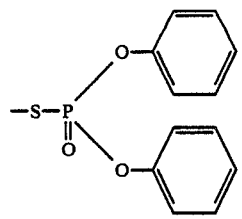 "
" " 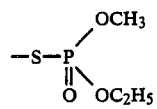 "
" " 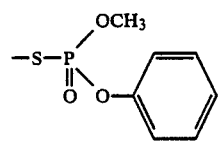 "
" " 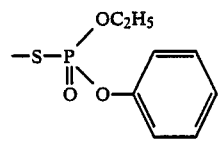 "
" " 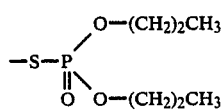 "
" " 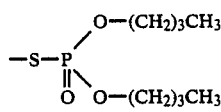 "
" " 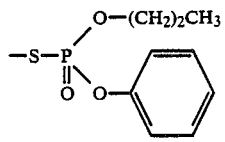 "
" " 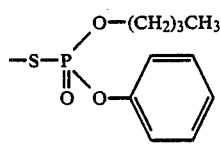 "
" " 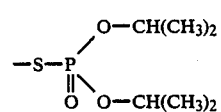 "
" Cl$_3$CCH$_2$— 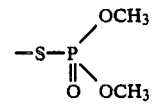 "
" " 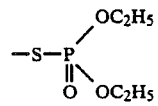 "

| | | | |
|---|---|---|---|
| " | " | 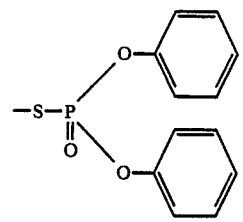 | " |
| " | " | 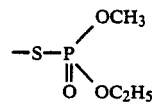 | " |
| " | " | 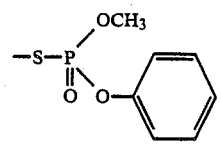 | " |
| " | " | 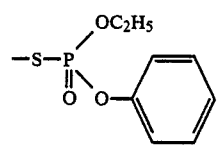 | " |
| " | " | 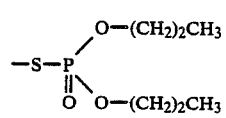 | " |
| " | " | 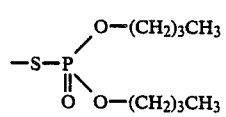 | " |
| " | " | 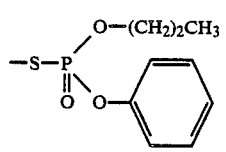 | " |
| " | " | 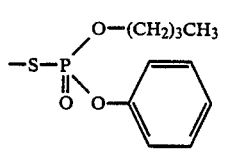 | " |
| " | " | 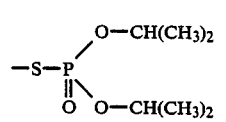 | " |
| " | (CH₃)₃C— | 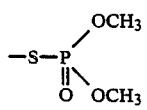 | " |
| " | " | 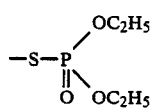 | " |

-continued
" " 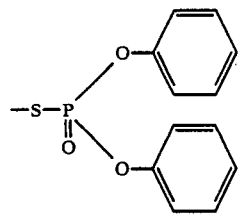 "
" " 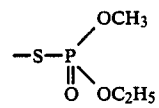 "
" " 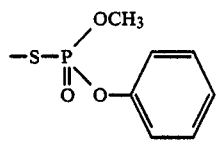 "
" " 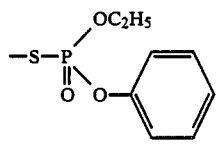 "
" " 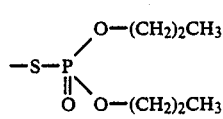 "
" " 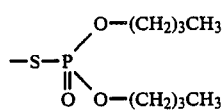 "
" " 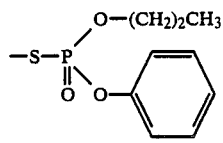 "
" " 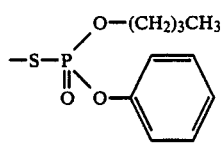 "
" " 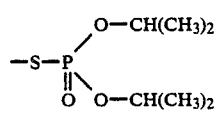 "
" 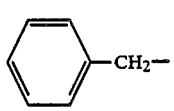 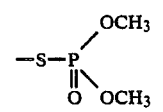 "
" " 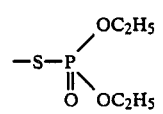 "

-continued
| " | " | 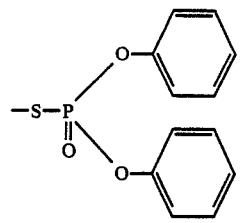 | " |
| " | " | 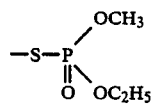 | " |
| " | " | 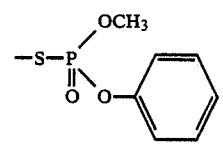 | " |
| " | " | 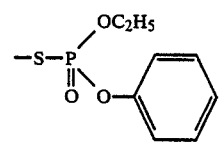 | " |
| " | " | 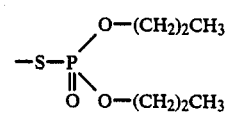 | " |
| " | " | 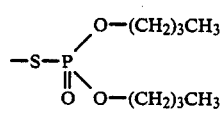 | " |
| " | " | 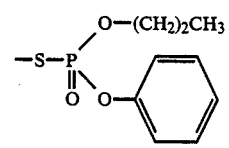 | " |
| " | " | 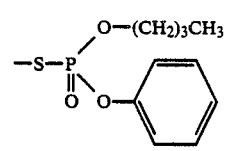 | " |
| " | " | 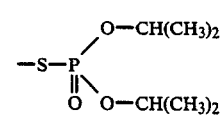 | " |
| " | 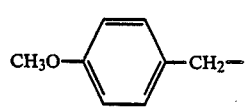 | 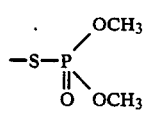 | " |
| " | " | 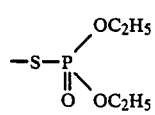 | " |

-continued
| | | | |
|---|---|---|---|
| " | " | 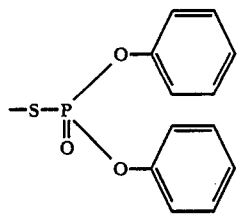 | " |
| " | " | 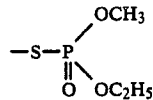 | " |
| " | " | 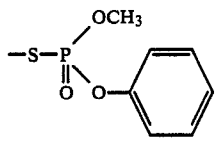 | " |
| " | " | 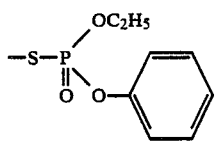 | " |
| " | " | 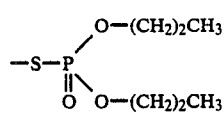 | " |
| " | " | 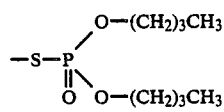 | " |
| " | " | 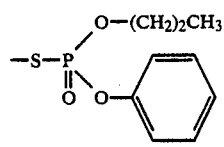 | " |
| " | " | 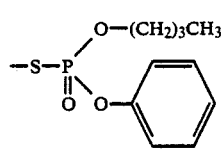 | " |
| " | " | 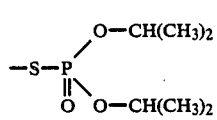 | " |
| " | 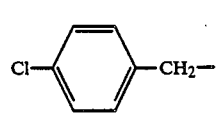 | 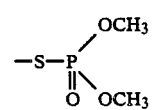 | " |
| " | " | 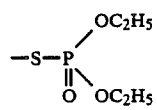 | " |

-continued
| " | " | 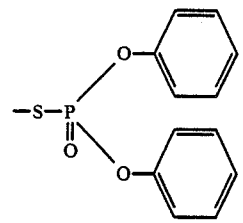 | " |
| " | " | 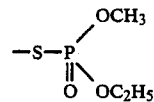 | " |
| " | " | 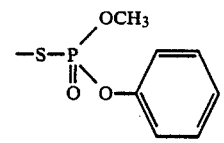 | " |
| " | " | 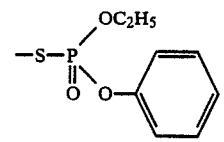 | " |
| " | " | 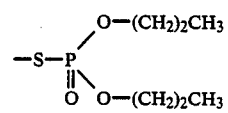 | " |
| " | " | 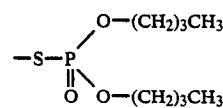 | " |
| " | " | 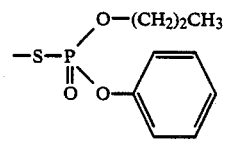 | " |
| " | " | 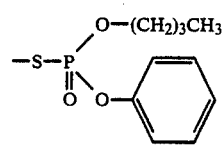 | " |
| " | " | 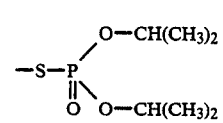 | " |
| 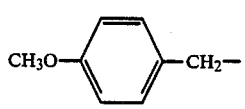 | " | 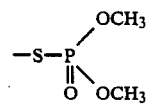 | " |
| " | " | 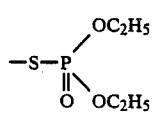 | " |

-continued
" " 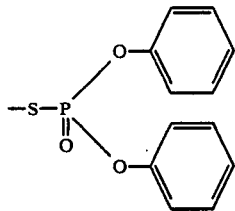 "
" " 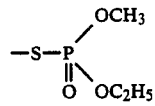 "
" " 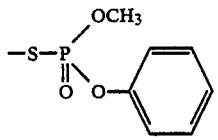 "
" " 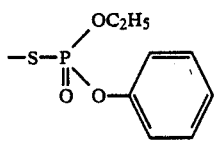 "
" " 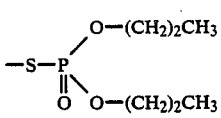 "
" " 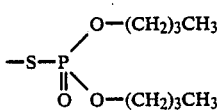 "
" " 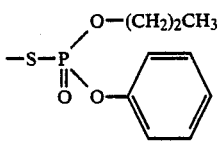 "
" " 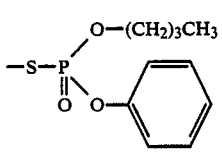 "
" " 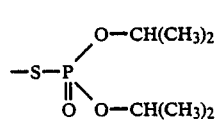 "
" ClCH₂CH₂— 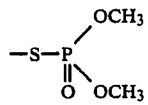 "
" " 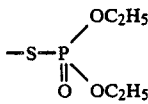 "

-continued
" " 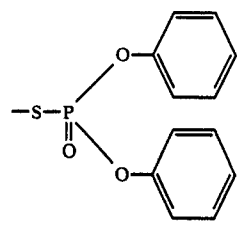 "
" " 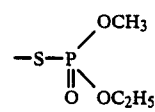 "
" " 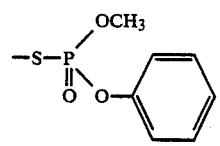 "
" " 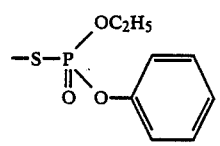 "
" " 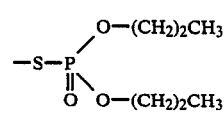 "
" " 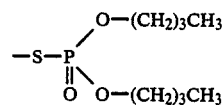 "
" " 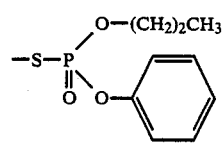 "
" " 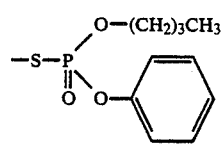 "
" " 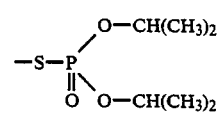 "
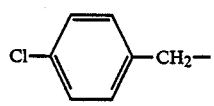 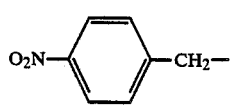 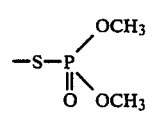 "
" " 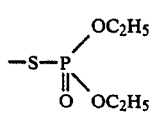 "

-continued
| | | | |
|---|---|---|---|
| " | " | 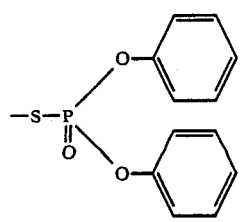 | " |
| " | " | 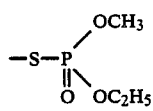 | " |
| " | " | 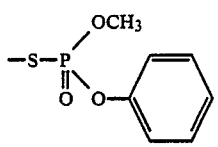 | " |
| " | " | 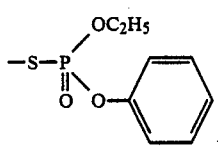 | " |
| " | " | 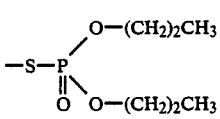 | " |
| " | " | 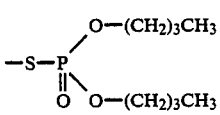 | " |
| " | " | 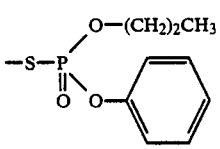 | " |
| " | " | 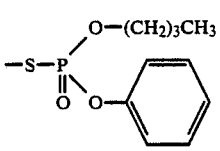 | " |
| " | " | 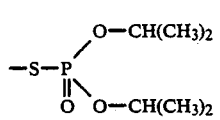 | " |
| 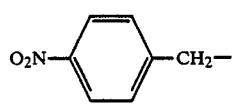 | 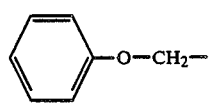 | 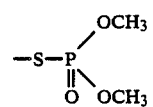 | " |
| " | " | 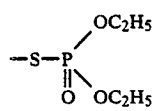 | " |

-continued
" " 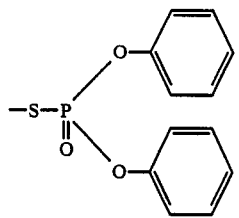 "
" " 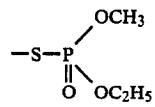 "
" " 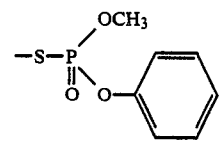 "
" " 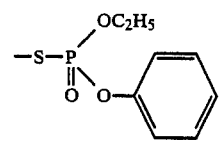 "
" " 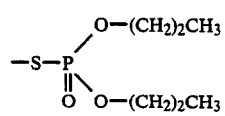 "
" " 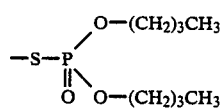 "
" " 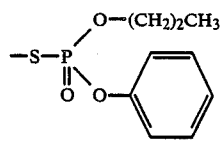 "
" " 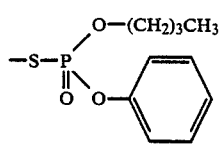 "
" " 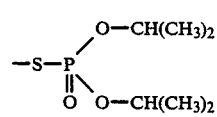 "
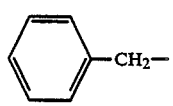 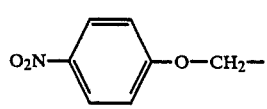 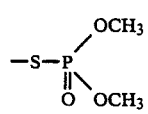 "
" " 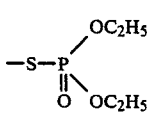 "

-continued
| | | | |
|---|---|---|---|
| " | " | 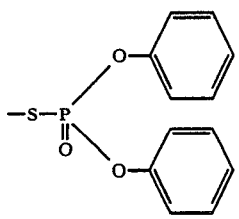 | " |
| " | " | 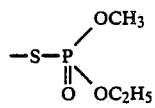 | " |
| " | " | 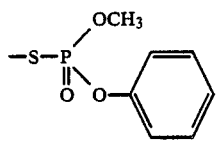 | " |
| " | " | 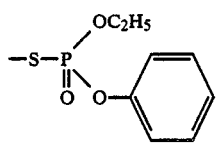 | " |
| " | " | 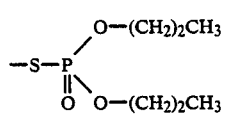 | " |
| " | " | 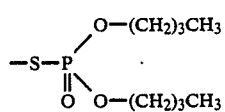 | " |
| " | " | 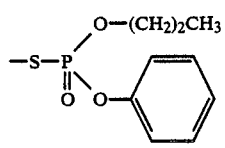 | " |
| " | " | 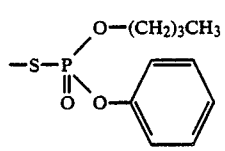 | " |
| " | " | 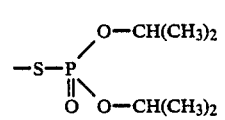 | " |
| 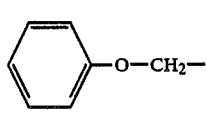 |  | 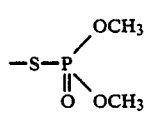 | " |
| " | " | 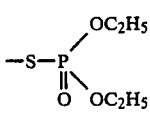 | " |

| " | " | 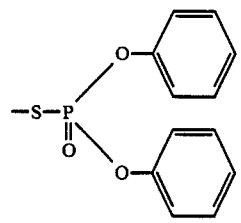 | " |
| " | " | 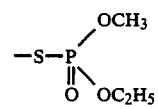 | " |
| " | " | 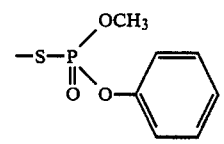 | " |
| " | " | 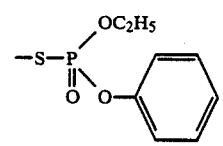 | " |
| " | " | 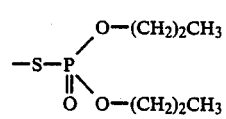 | " |
| " | " | 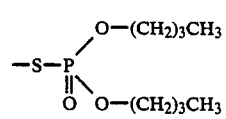 | " |
| " | " | 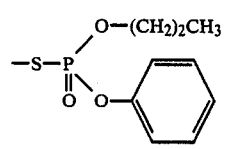 | " |
| " | " | 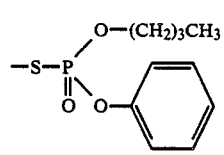 | " |
| " | " | 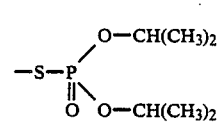 | " |
| " | 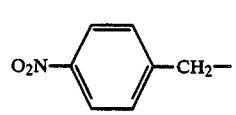 | 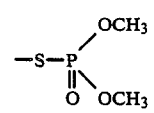 | " |
| " | " | 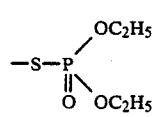 | " |

-continued
| | | | |
|---|---|---|---|
| " | " | 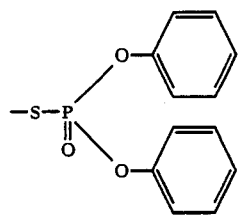 | " |
| " | " | 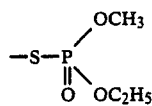 | " |
| " | " | 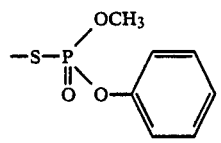 | " |
| " | " | 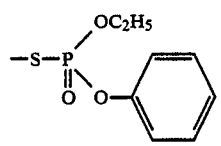 | " |
| " | " | 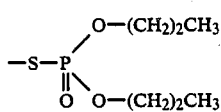 | " |
| " | " | 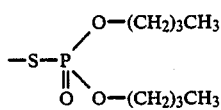 | " |
| " | " | 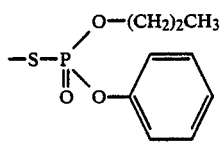 | " |
| " | " | 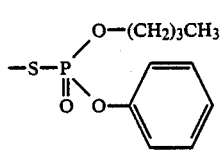 | " |
| " | " | 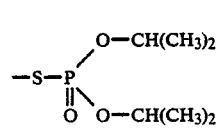 | " |
| " | 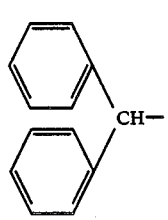 | 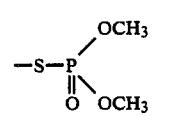 | " |
| " | " | 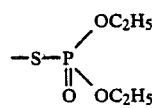 | " |

-continued
| | | |
|---|---|---|
| " | " | 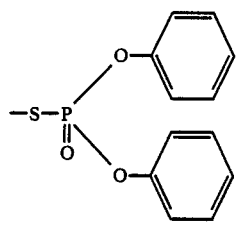 " |
| " | " | 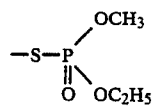 " |
| " | " | 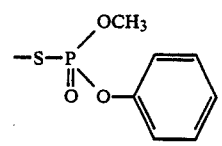 " |
| " | " | 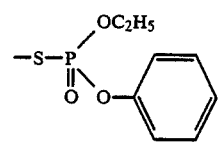 " |
| " | " | 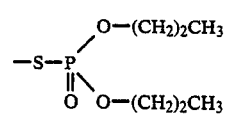 " |
| " | " | 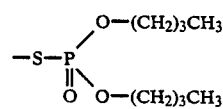 " |
| " | " | 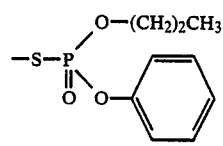 " |
| " | " | 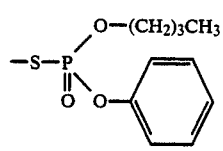 " |
| " | " | 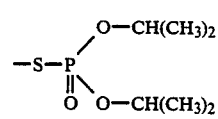 " |
| " | 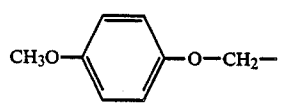 | 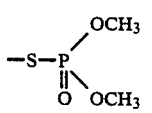 " |
| " | " | 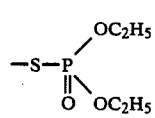 " |

-continued
| | | | |
|---|---|---|---|
| " | " | 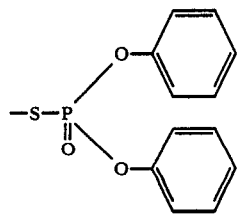 | " |
| " | " | 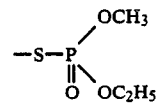 | " |
| " | " | 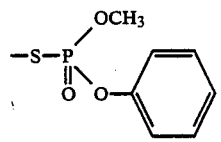 | " |
| " | " | 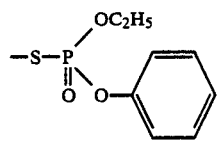 | " |
| " | " | 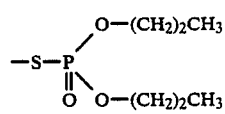 | " |
| " | " | 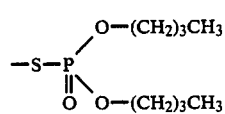 | " |
| " | " | 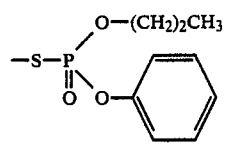 | " |
| " | " | 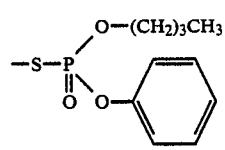 | " |
| " | " | 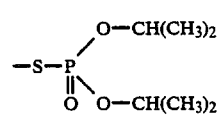 | " |
| 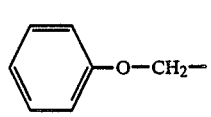 | Cl$_3$CCH$_2$— | 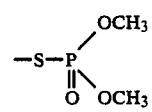 | " |
| " | " | 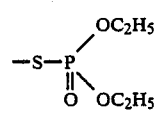 | " |

-continued
| " | " | 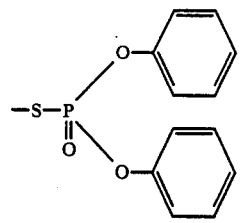 | " |
| " | " | 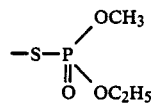 | " |
| " | " | 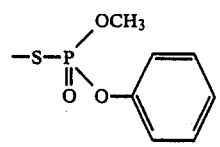 | " |
| " | " | 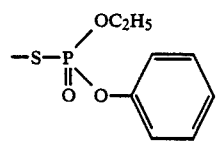 | " |
| " | " | 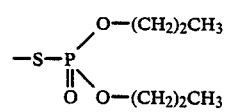 | " |
| " | " | 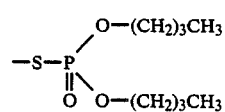 | " |
| " | " | 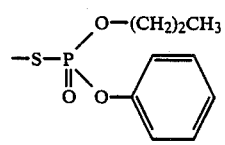 | " |
| " | " | 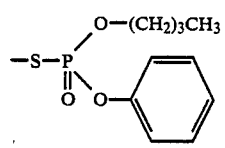 | " |
| " | " | 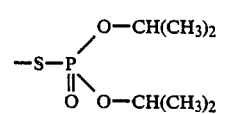 | " |
| " | (CH$_3$)$_3$C— | 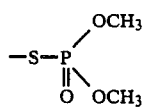 | " |
| " | " | 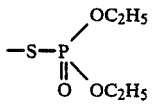 | " |

-continued
| " | " | 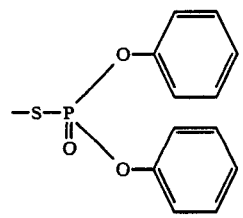 | " |
| " | " | 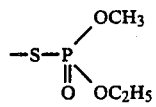 | " |
| " | " | 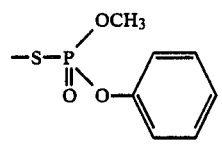 | " |
| " | " | 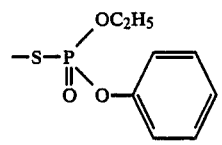 | " |
| " | " | 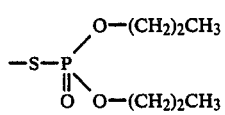 | " |
| " | " | 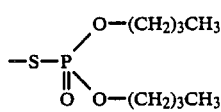 | " |
| " | " | 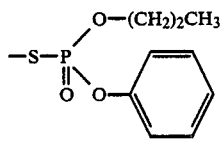 | " |
| " | " | 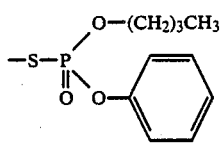 | " |
| " | " | 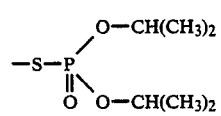 | " |
| " | 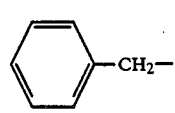 | 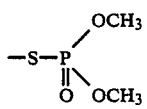 | " |
| " | " | 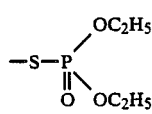 | " |

-continued
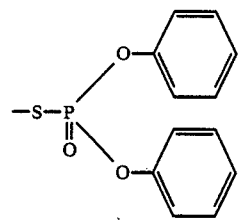
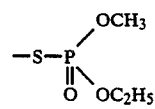
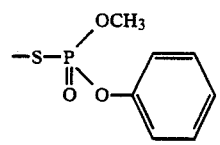
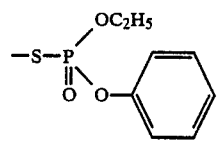
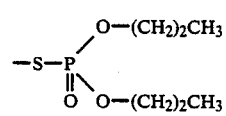
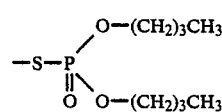
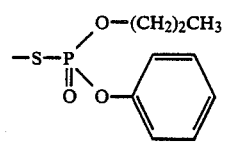
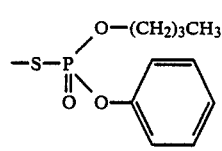
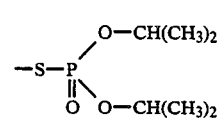
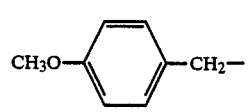 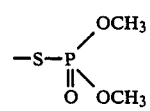
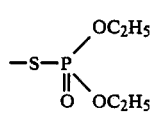

-continued
" " 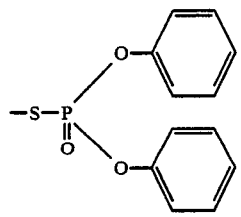 "
" " 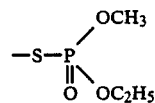 "
" " 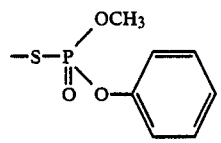 "
" " 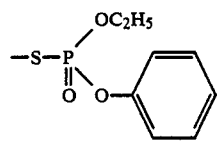 "
" " 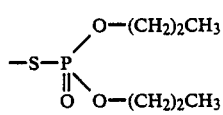 "
" " 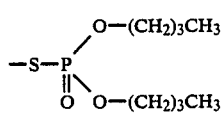 "
" " 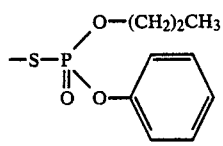 "
" " 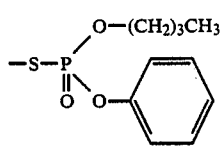 "
" " 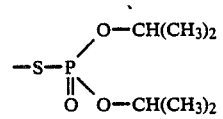 "
" 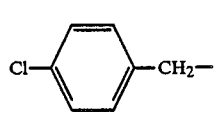 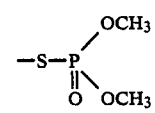 "
" " 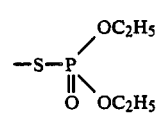 "

-continued
" " 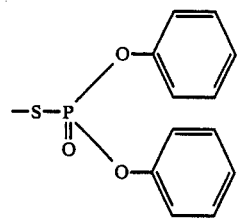 "
" " 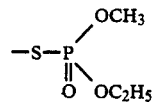 "
" " 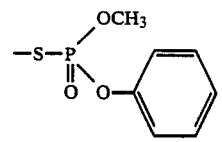 "
" " 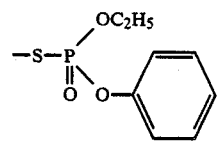 "
" " 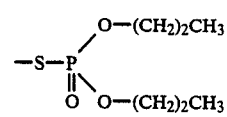 "
" " 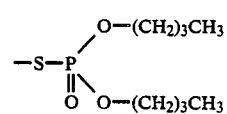 "
" " 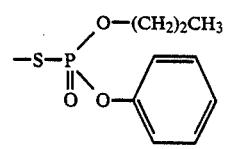 "
" " 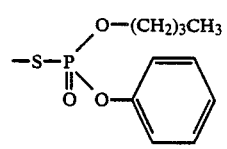 "
" " 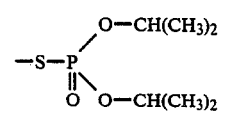 "
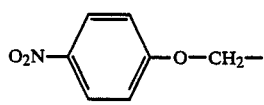 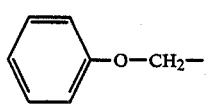 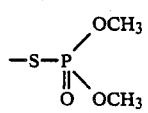 "
" " 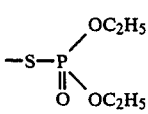 "

-continued
" " 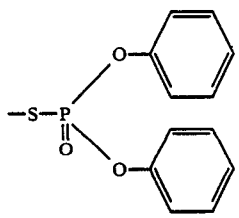 "
" " 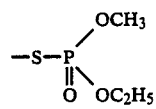 "
" " 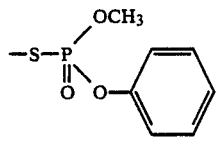 "
" " 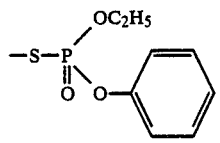 "
" " 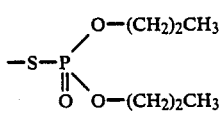 "
" " 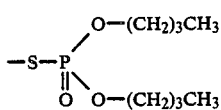 "
" " 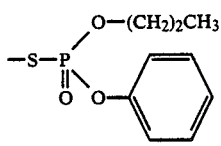 "
" " 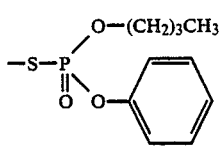 "
" " 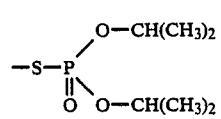 "
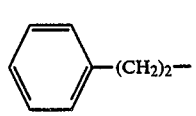 CH$_3$— 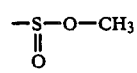 "
" 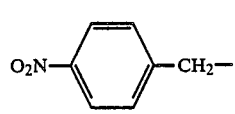 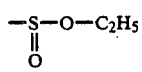 "

-continued
| | | | |
|---|---|---|---|
| 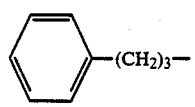 | 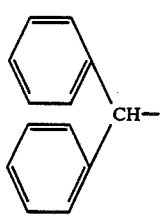 | 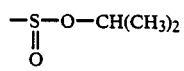 | " |
| 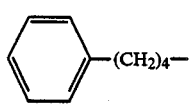 | ClCH₂CH₂— | 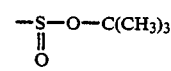 | Br |
| 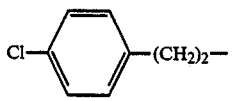 | 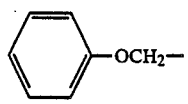 | 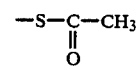 | " |
| 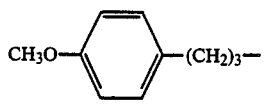 | 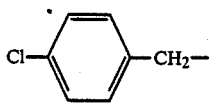 | 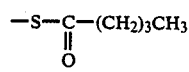 | " |
| 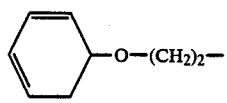 | ClCH₂CH₂— | 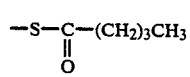 | " |
| 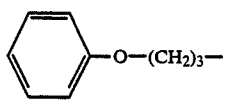 | 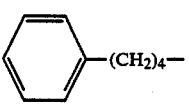 | 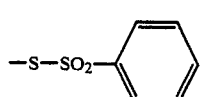 | I |
| 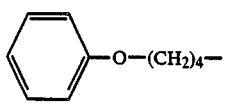 | 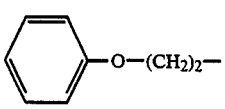 | 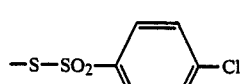 | " |
| 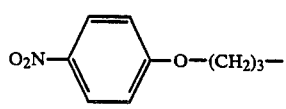 |  | 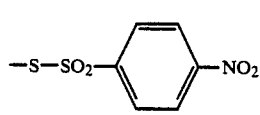 | " |
| 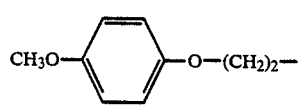 | Cl₃CCH₂— | 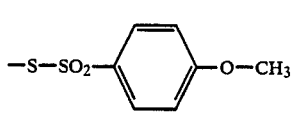 | " |
| 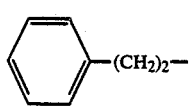 | CH₃— | 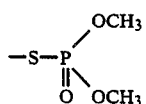 | Br |
| " | 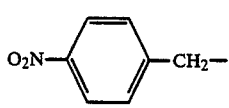 | 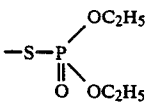 | " |
| 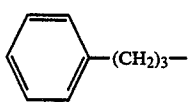 |  | 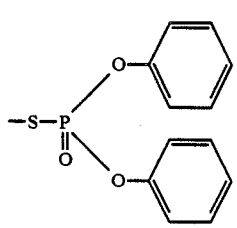 | " |

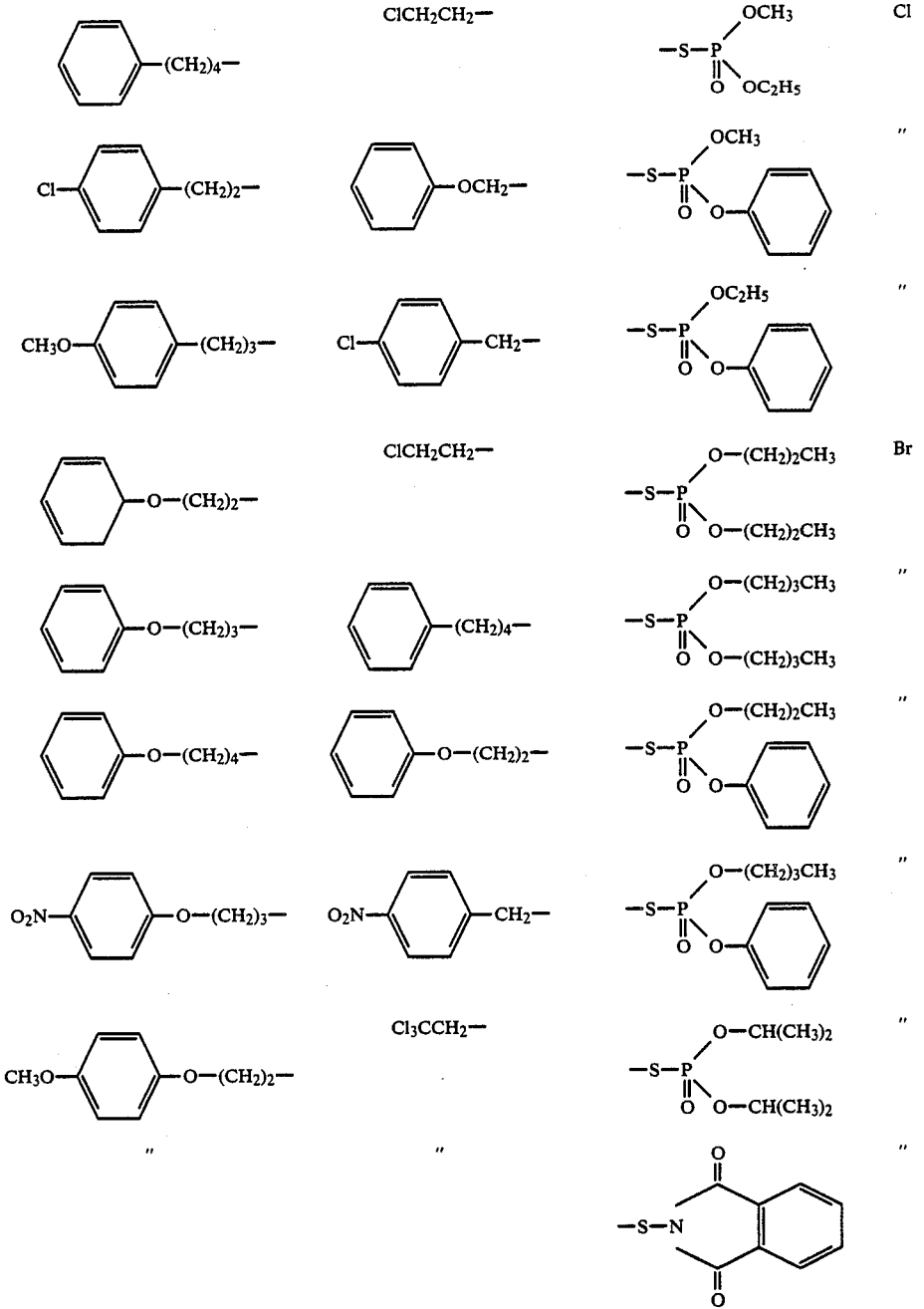

The compounds of the formulae (Ib), (Ic) and (Id) are all novel compounds heretofore undisclosed in literature.

The azetidione derivatives of the formula (I) can be prepared by various processes. Examples of the processes are hereinafter stated.

The compounds of the formula (Ia) wherein $R^3$ is $$-\overset{O}{\underset{\|}{S}}-O-R^4,$$

namely the compounds of the formula (Ic), can be produced for example by subjecting to electrolysis an azetidione derivative of the formula wherein $R^1$ and $R^2$ are as defined above in a lower alcohol.

The compounds of the formula (II) useful as the starting material are known and can be prepared by the process for example described in Tetrahedron Letters 3001 (1973).

The compound of the formula (II) is electrolyzed in the presence of lower alcohol by passing the required amount of current through the solution. Examples of useful lower alcohols are methanol, ethanol, propanol, isopropanol, butanol, tert-butyl alcohol, etc. According to the present invention, these lower alcohols, which are usually used as solvents, are usable in admixture with any other suitable solvent. Useful solvents to be admixed with the lower alcohol include tetrahydrofuran, diethyl ether, dioxane and like ethers, acetonitrile, propionitrile and like nitriles, methylene chloride, chloroform, carbon tetrachloride, dichloroethane and like hydrocarbon halides or mixtures thereof.

It is preferred to incorporate a supporting electrolyte in the reaction system. Useful supporting electrolytes include sulfuric acid, perchloric acid, phosphoric acid and like mineral acids, p-toluenesulfonic acid, methanesulfonic acid and like sulfonic acids, formic acid, acetic acid, propionic acid and like organic acids, etc.

The electrysis of the compound (II) can be performed at either controlled potential or constant current. The cathode current density is usually in the range of about 1 to about 500 mA/cm$^2$, preferably about 5 to about 200 mA/cm$^2$. The required amount of electric charge is usually about 2 to about 50 F, preferably about 3 to about 40 F, per mole of the starting material, although variable depending on the concentration of the substrate, the kind of the solvent, the type or shape of the electrolytic bath, etc. Useful electrodes include those usually used, such as those of platinum, carbon, stainless steel, titanium, nickel or the like. The reaction temperature is not particularly limited as far as it is below a level at which there occurs the decomposition or conversion of the starting material and reaction product. It ranges usually from about −70° to about 80° C., preferably from about −30° to about 60° C., most preferably about −20° to about 30° C. The electrolytic bath is used with or without a diaphragm.

The compounds of the formula (Ia) wherein R$^3$ is

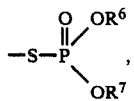

namely the compounds of the formula (Id), are prepared by reacting the azetidinone derivative of the formula (II) with the ester of phosphorous acid represented by the formula

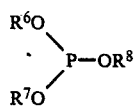
(III)

wherein R$^8$ is lower alkyl or phenyl and R$^6$ and R$^7$ are as defined above. The esters of phosphorous acid having the formula (III) are known and readily available. Examples of the compounds (III) are trimethylphosphite, triethylphosphite, triphenylphosphite, methyldiethylphosphite, dimethylethylphosphite, methyldiphenylphosphite, dimethylphenylphosphite, diethylphenylphosphite, tri-(n-propyl)phosphite, tri-(n-butyl)phosphite, di-(n-propyl)phenylphosphite, di-(n-butyl)phenylphosphite, etc.

According to the present invention, the reaction between the compounds of the formulae (II) and (III0 is carried out without a solvent or with a suitable inert solvent. Useful inert solvents are, for example, methylene chloride, chloroform, carbon tetrachloride, dichloroethane and like hydrocarbon halides, diethyl ether, dibutyl ether, dioxane, tetrahydrofuran and like ethers, acetonitrile, butyronitrile and like nitriles, benzene, toluene, chlorobenzene and like aromatic hydrocarbons, hexane, cyclohexane, heptane, pentane and like hydrocarbons and mixtures thereof, etc. The amount of the compound having the formula (III) relative to that of the compound (II), is not particularly limited but widely variable. The compound of the formula (III) is used in an amount of usually about 0.1 to about 10 moles, preferably about 1.5 to about 3 moles, per mole of the compound (II). The reaction is effected at any of ambient, increased and reduced temperatures, usually at about −30° about 100° C., preferably about −20° to 80° C.

The compounds of the formula (Ia) wherein R$^3$ is

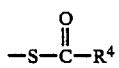

cam be prepared by the process disclosed in Japanese Unexamined Patent Publication No. 102669/1974. Similarly those wherein R$^3$ is

can be produced by the process taught by Tetrahedron Letters 3001 (1973) and those wherein R$^3$ is

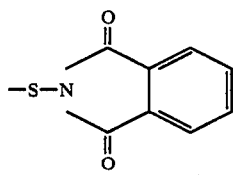

by the process described in Tetrahedron Letters 4897 (1970).

The compounds of the formula (Ib) are produced by subjecting the compound of the formula (Ia) to electrolysis in the presence of hydrohalogenic acid and/or halide.

Useful hydrohalogenic acids include a wide variety of known compounds such as hydrochloric acid, hydrobromic acid, hydroiodic acid, among which the hydrochloric acid is preferred. Usable as the halide are various compounds such as ammonium chloride, tetramethylammonium chloride, benzyltrimethylammonium chloride and like quaternary ammonium chlorides, lithium chloride, sodium chloride, potassium chloride and like alkali metal chlorides, magnesium chloride, barium chloride, calcium chloride and like alkaline earth metal chlorides and other chlorides, ammonium bromide, tetramethylammonium bromide, tetraethylammonium bromide, benzyltrimethylammonium bromide and like quaternary ammonium bromides, sodium bromide, cerium bromide, lithium bromide and like alkali metal bromides, magnesium bromide and like alkaline earth metal bromides and other bromides, ammonium iodide, tetramethylammonium iodide, tetraethylammonium iodide and like quaternary ammonium iodides, lithium iodide, potassium iodide, sodium iodide and like alkali metal iodides and like other iodides, etc. The amounts of the hydrohalogenic acid and/or halide to be used are not particularly limited but widely variable. They are usually used in an amount of about 0.5 to about 10 moles, preferably about 1 to about 8 moles, per mole of the compound having the formula (Ia). The halide is effective when used in conjunction with mineral acid or organic acid. Examples of useful mineral acids are sulfuric acid, sodium hydrogensulfate, potassium hydrogensulfate, phosphorica acid, boric acid, etc. Useful organic acids include formic acid, acetic acid, propionic acid, butyric acid, oxalic acid, citric acid and like carboxylic acid, p-toluenesulfonic acid, methanesulfonic acid and like sulfonic acids, etc. It is preferred to use the mineral acid or organic acid in an amount of about 0.5 to about 10 mole, preferably about 1 to about 8 mole, per mole of the compound (Ia). Generally used as the reaction medium is water, organic solvent or a mixture thereof. Usable as the organic solvent are various solvents inert to halogenation such as methyl formate, ethyl formate, methyl acetate, ethyl acetate, butyl acetate, ethyl propionate and like esters, dichloromethane, chloroform, carbon tetrachloride, dichloroethane, dibromoethane, chlorobenzene and like hydrocarbon halides, diethyl ether, dibutyl ether, dioxane, tetrahydrofuran and like ethers, acetonitriles, butyronitriles and like nitriles, pentane, hexane, cyclohexane and like hydrocarbons, carbon disulfide, etc.

The electrolysis of the compound (Ia) can be performed at either controlled potential or constant current. The cathode current density is usually in the range of about 1 to about 500 mA/cm$^2$, preferably about 5 to about 200 mA/cm$^2$. The required amount of electric charge is usually about 2 to about 50 F, preferably about 3 to about 40 F, per mole of the starting material, although variable depending on the concentration of the substrate, the kind of the solvent, the type or shape of the electrolytic bath, etc. Useful electrodes include those usually used, such as those of platinum, carbon, stainless steel, titanium, nickel or the like. The reaction temperature is not particularly limited as far as it is below a level at which there occurs the decomposition or conversion of the starting material and reaction product. It is usually about −30° to about 60° C., preferably about −20° to about 30° C. The electrolytic bath is used with or without a diaphragm.

The compounds of this invention are each readily separated from the reaction mixture and purified by the usual means such as solvent extraction, column chromatography, etc.

According to the processes stated above, the end product as contemplated can be prepared in a high yield by a simplified procedure under moderate conditions. Further the processes of this invention facilitate the separation and purification of the compounds and are free from the problem arising from the disposal of by-products. Therefore, the present processes are extremely advantageous from commercial points of view.

The compounds of the formula (I) are useful as the intermediates for the synthesis of penicillin- and cephalosporin-type antibiotics. For example, cephalosporin compounds (IV) useful as antibiotic agents can be derived from the compounds of the formula (Ib) according to the following reaction formula in which $R^1$, $R^2$, $R^3$ and $X'$ are as defined above.

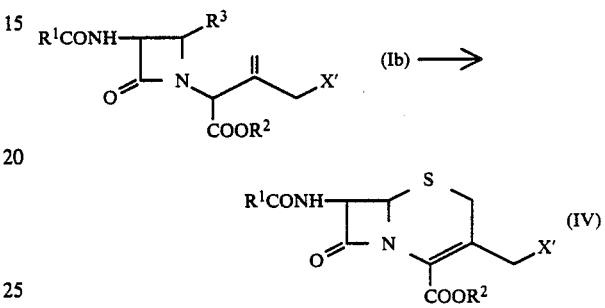

The compound of the formula (Ia) is advantageously used as the intermediate for the synthesis of compound of the formula (Ib) from which the compound of the formula (IV) is derived as the end product.

In the course of the reaction, a base is permitted to act on the compound of the formula (Ib) in the presence of an organic solvent, whereby the compound of the formula (IV) is prepared.

Exemplary of useful organic solvents are methanol, ethanol, isopropanol and like alcohols, acetonitrile, butyronitrile and like nitriles, acetone, methyl ethyl ketone and like ketones, formamide dimethylformamide, diethylformamide, dimethylacetamide and like amides, etc. These solvents are used singly or in mixture. It is preferred to use polar solvents singly or in admixture, such as formamide, diethylformamide, dimethylacetamide, etc. Useful bases are for example potassium hydroxide, sodium hydroxide and like metal hydroxides, potassium acetate, sodium acetate and like alkali metal salts of carboxylic acids, triethylamine, 1,8-diazabicyclo[5,4,0]7-undecene, 1,5-diazabicyclo[4,3,0]5-nonenepyridine and like amines, potassium iodide, sodium iodide and like alkali metal halides, ammonia, ammonia water and the like among which ammonia and ammonia water are preferred. The amount of the base to be used is not particularly limited but is determined over a wide range. The base is used in an amount of usually about 0.1 to about 10 moles, preferably about 1 to about 1.5 moles, per mole of the compound (Ib). The reaction temperature is in the range of usually about −78° to about 40° C., preferably about −50° to about 5° C. The reaction time is variable depending on the reaction temperature and the type of starting material, but the reaction usually takes about 5 minutes to about 10 hours to go to completion.

The compound of the formula (IV) thus preprared is easily separated from the reaction mixture and purified by the usual means such as solvent extraction, column chromatography, etc.

The foregoing processes of the present invention are able to produce the compounds of the formula (IV) in high yields with high purity by a simplified procedure.

For a better understanding of the invention examples are given below.

EXAMPLE 1

A 250.3 mg quantity of a compound (II) wherein $R^1$ is benzyl and $R^2$ is methyl was dissolved in 50 ml of methanol. To the solution was added 0.4 ml of concentrated sulfuric acid. Electrolysis was continued for 2 hours with stirring at a temperature of 0° to 2° C. and a cathode current density of 5 mA/cm² by using platinum electrodes (4×3 cm²). After the completion of the reaction, the reaction mixture was extracted with ethyl acetate, washed with a saturated aqueous solution of sodium hydrogencarbonate and then with a saturated aqueous solution of sodium chloride and dried over anhydrous sodium sulfate. The solvent was removed from the dried product at reduced pressure. The residue was separated and purified by silica gel column chromatography by using a 3:1 benzene-ethyl acetate mixture as a developer, giving 167.9 mg of a compound (Ic) wherein $R^1$ is benzyl and $R^2$ and $R^4$ are both methyl. Yield 88%.

NMR (CDCl₃, δ, ppm): 1.99 (s, 3H), 3.42 (s, 3H), 3.56 (s, 2H), 3.72 (s, 3H), 4.52 (q, 1H), 4.70, 4.84, 5.05, 5.16 (4s, 4H), 6.71 (d, 1H), 7.27 (s, 5H).

EXAMPLE 2

A 50.2 mg quantity of a compound (II) wherein $R^1$ is benzyl and $R^2$ is methyl was dissolved in 4 ml of methanol and 4.5 ml of tetrahydrofuran. To the solution was added 0.07 ml of concentrated sulfuric acid. By using platinum electrodes, electrolysis was continued for 1 hour and 35 minutes at a temperature of −14° to −12° C. and a cathode current density of 5 mA/cm². After the reaction was completed, the subsequent procedure of Example 1 was repeated, giving 30.2 mg of a compound (Ic) wherein $R^1$ is benzyl and $R^2$ and $R^4$ are both methyl. Yield 79%.

The compound thus obtained was identified by IR and NMR.

EXAMPLE 3

A 50.6 mg quantity of a compound (II) wherein $R^1$ is benzyl and $R^2$ is methyl was dissolved in 8 ml of methanol. To the solution were added 0.07 ml of concentrated sulfuric acid. By using carbon electrodes, electrolysis was continued for 45 minutes at a temperature of 0° to 2° C. and a cathode current density of 10 mA/cm². After the completion of the reaction, the subsequent procedure described in Example 1 produced 30.2 mg of a compound (Ic) wherein $R^1$ is benzyl and $R^2$ and $R^4$ are both methyl. Yield 77%.

The compound thus prepared was identified with IR and NMR.

EXAMPLE 4

A 49.5 mg quantity of a compound (II) wherein $R^1$ is benzyl and $R^2$ is methyl was dissolved in 8 ml of methanol. To the solution were added 0.07 ml of concentrated sulfuric acid and 42 mg of copper sulfate. By using platinum electrodes, electrolysis was continued for 1 hour and 15 minutes at a temperature of 0° to 2° C. and a cathode current density of 10 mA/cm². During the electrolysis, the direction of current was altered every 30 seconds. After the completion of the reaction, the subsequent procedure of Example 1 produced 32.07 mg of a compound (Ic) wherein $R^1$ is benzyl and $R^2$ and $R^4$ are both methyl. Yield 84%.

The compound thus obtained was identified by IR and NMR.

EXAMPLES 5 TO 24

Using the compounds (II) as the starting material wherein $R^1$ and $R^2$ are as defined in Table 1 below, the same procedure as in Examples 1 was repeated, affording compounds exhibiting properties (IR and NMR) shown in Table 1 and having the formula

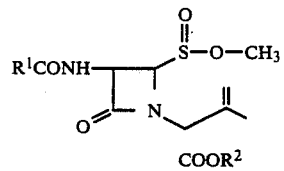

wherein $R^1$ and $R^2$ are as defined below in Table 1 and Ph is phenyl (the same in subsequent tables given hereinafter).

TABLE 1

| Example | $R^1$ | $R^2$ | IR (cm⁻¹) | NMR (δ, ppm) |
|---|---|---|---|---|
| 5 | PhCH₂— | CH₃ | 1775<br>1735<br>1670 | 1.89 (s, 3H), 3.42 (s, 3H), 3.56 (s, 2H),<br>3.72 (s, 3H), 4.52 (d, J=6.2Hz, 1H),<br>4.70 (s, 1H), 4.84 (s, 1H), 5.05 (s, 1H),<br>5.15 (s, 1H), 6.70 (d, J=6.2Hz, 1H),<br>7.27 (s, 5H) |
| 6 | PhCH₂— | —CH₂—⟨C₆H₄⟩—NO₂ | 1780<br>1741<br>1669 | 1.86 (s, 3H), 3.42 (s, 3H), 3.56 (s, 2H),<br>4.52 (d, J=6.2Hz, 1H), 4.65 (s, 1H),<br>4.79 (s, 1H), 5.02 (s, 1H), 5.16 (s, 1H),<br>5.18 (s, 2H), 6.5 (d, J=6.2Hz, 1H),<br>7.26 (s, 5H), 7.50 (d, 9.5Hz, 2H),<br>8.20 (d, 9.5Hz, 2H) |

TABLE 1-continued

| Example | R¹ | R² | IR (cm⁻¹) | NMR (δ, ppm) |
|---|---|---|---|---|
| 7 | PhCH₂— | —CH(Ph)(Ph) | 1780, 1745, 1675 | 1.79 (s, 3H), 3.43 (s, 3H), 3.52 (s, 3H), 4.49 (d, J=6.2Hz, 1H), 4.63 (s, 1H), 4.77 (s, 1H), 4.98 (s, 1H), 5.10 (s, 1H), 6.3 (d, J=6.2Hz, 1H), 6.92 (s, 1H), 7.0–8.0 (m, 15H) |
| 8 | PhCH₂— | —CH₂CCl₃ | 1778, 1735, 1680 | 1.89 (s, 3H), 3.40 (s, 3H), 3.66 (s, 2H), 4.52 (d, J=6.2Hz, 1H), 4.75 (bs, 3H), 4.89 (s, 1H), 5.10 (s, 1H), 5.16 (s, 1H), 6.6 (d, J=6.2Hz, 1H), 7.29 (s, 5H) |
| 9 | PhCH₂— | tert-C₄H₉ | 1768, 1730, 1675 | 1.45 (s, 9H), 1.85 (s, 3H), 3.42 (s, 3H), 3.55 (s, 2H), 4.50 (d, J=6.2Hz, 1H), 4.68 (s, 1H), 4.83 (s, 1H), 5.03 (s, 1H), 5.16 (s, 1H), 6.5 (d, J=6.2Hz, 1H), 7.28 (s, 5H), |
| 10 | PhOCH₂— | CH₃— | 1776, 1740, 1680 | 1.95 (s, 3H), 3.43 (s, 3H), 3.76 (s, 3H), 4.53 (s, 2H), 4.62 (d, J=6.2Hz, 1H), 4.70 (s, 1H), 4.84 (s, 1H), 5.06 (s, 1H), 5.27 (s, 1H), 6.5–7.5 (m, 6H) |
| 11 | PhOCH₂— | —CH₂—C₆H₄—NO₂ | 1780, 1745, 1690 | 1.97 (s, 3H), 3.44 (s, 3H), 4.52 (s, 2H), 4.61 (d, J=6.2Hz, 1H), 4.66 (s, 1H), 4.79 (s, 1H), 5.02 (s, 1H), 5.19 (s, 2H), 5.24 (s, 1H), 6.5–8.4 (m, 10H) |
| 12 | PhOCH₂— | —CH(Ph)(Ph) | 1780, 1743, 1688 | 1.90 (s, 3H), 3.43 (s, 3H), 4.49 (s, 2H), 4.57 (d, J=6.2Hz, 1H), 4.63 (s, 1H), 4.77 (s, 1H), 4.99 (s, 1H), 5.22 (s, 1H), 6.5–8.0 (m, 17H) |
| 13 | PhOCH₂— | —CH₂CCl₃ | 1780, 1742, 1680 | 1.95 (s, 3H), 3.41 (s, 3H), 4.53 (s, 2H), 4.63 (m, 2H), 4.77 (m, 3H), 5.01 (s, 1H), 5.26 (s, 1H), 6.5–7.5 (m, 6H) |
| 14 | PhOCH₂— | tert-C₄H₉— | 1778, 1740, 1667 | 1.47 (s, 9H), 1.94 (s, 3H), 3.44 (s, 3H), 4.54 (s, 2H), 4.62 (d, J=6.2Hz, 1H), 4.71 (s, 1H), 4.84 (s, 1H), 5.05 (s, 1H), 5.26 (s, 1H), 6.5–7.5 (m, 6H) |
| 15 | PhCH₂— | CH₃— | 1780, 1760, 1675 | 3.40 (s, 3H), 3.52 (s, 2H), 3.71 (s, 3H), 4.20 (bs, 2H), 4.46 (d, J=7Hz, 1H), 4.82 (s, 1H), 4.95 (s, 1H), 5.33 (s, 1H), 5.52 (s, 1H), 6.42 (d, J=7Hz, 1H), 7.23 (s, 5H) |
| 16 | PhCH₂— | —CH₂—C₆H₄—NO₂ | 1780, 1755, 1675 | 3.41 (s, 3H), 3.52 (s, 2H), 4.20 (bs, 2H), 4.46 (d, J=7Hz, 1H), 4.77 (s, 1H), 4.90 (s, 1H), 5.18 (s, 2H), 5.29 (s, 1H), 5.52 (s, 1H), 6.50 (d, J=7Hz, 1H), 7.25 (s, 5H), 7.48 (d, 9.5Hz, 2H), 8.17 (d, 9.5Hz, 2H) |
| 17 | PhCH₂— | —CH(Ph)(Ph) | 1775, 1755, 1673 | 3.42 (s, 3H), 3.47 (s, 2H), 4.24 (bs, 2H), 4.41 (d, J=7Hz, 1H), 4.73 (s, 1H), 4.88 (s, 1H), 5.26 (s, 1H), 5.47 (s, 1H), 6.44 (d, J=7Hz, 1H), 6.92 (s, 1H), 7.0–8.0 (m, 15H) |
| 18 | PhCH₂— | —CH₂CCl₃ | 1785, 1760, 1678 | 3.38 (s, 3H), 3.62 (s, 2H), 4.30 (bs, 2H), 4.51 (d, J=7Hz, 1H), 4.80 (bs, 2H), 4.87 (s, 1H), 5.00 (s, 1H), 5.38 (s, 1H), 5.52 (s, 1H), 6.3 (d, J=7Hz, 1H), 7.3 (s, 5H) |
| 19 | PhCH₂— | tert-C₄H₉— | 1772, 1763, 1665 | 1.47 (s, 9H), 3.40 (s, 3H), 3.51 (s, 2H), 4.18 (bs, 2H), 4.44 (d, J=7Hz, 1H), 4.79 (s, 1H), 4.94 (s, 1H), 5.31 (s, 1H), 5.52 (s, 1H), 6.6 (d, J=7Hz, 1H), 7.24 (s, 5H) |
| 20 | PhOCH₂— | CH₃— | 1785, 1760, 1683 | 3.42 (s, 3H), 3.55 (s, 3H), 4.22 (bs, 2H), 4.56 (d, 7Hz, 1H), 4.52 (s, 2H), 4.85 (s, 1H), 4.97 (s, 1H), 5.35 (s, 1H), 5.54 (s, 1H), 6.5–7.5 (m, 6H) |
| 21 | PhOCH₂ | —CH₂—C₆H₄—NO₂ | 1773, 1756, 1668 | 3.43 (s, 3H), 4.24 (bs, 2H), 4.55 (d, 7Hz, 1H), 4.53 (s, 2H), 4.80 (s, 1H), 5.02 (s, 1H), 5.20 (s, 2H), 5.30 (s, 1H), 5.54 (s, 1H), 6.45 (d, J=7Hz, 1H), 6.8–8.3 (m, 9H) |

TABLE 1-continued

| Example | R¹ | R² | IR (cm⁻¹) | NMR (δ, ppm) |
|---|---|---|---|---|
| 22 | PhOCH₂— | —CH(Ph)(Ph) | 1783<br>1754<br>1678 | 3.43 (s, 3H), 4.26 (bs, 2H),<br>4.51 (d, J=7Hz, 1H), 4.47 (s, 2H),<br>4.80 (s, 1H), 4.91 (s, 1H), 5.29 (s, 1H),<br>5.49 (s, 1H), 6.3 (d, J=7Hz, 1H),<br>6.91 (s, 1H), 7.0–8.0 (m, 15H) |
| 23 | PhOCH₂— | —CH₂CCl₃ | 1780<br>1765<br>1690 | 3.41 (s, 3H), 4.23 (bs, 2H),<br>4.58 (d, 7Hz, 1H), 4.57 (s, 2H),<br>4.75 (bs, 2H), 4.90 (s, 1H), 5.02 (s, 1H),<br>5.40 (s, 1H), 5.53 (s, 1H),<br>6.6–7.5 (m, 6H) |
| 24 | PhOCH₂— | tert-C₄H₉— | 1785<br>1758<br>1680 | 1.45 (s, 9H), 3.40 (s, 3H), 4.21 (bs, 2H),<br>4.53 (m, 3H), 4.82 (s, 1H), 4.96 (s, 1H),<br>5.33 (s, 1H), 5.50 (s, 1H), 6.6–7.5 (m, 6H) |

EXAMPLE 25

A 100 mg quantity of a compound (II) wherein R¹ is phenoxymethyl and R² is methyl was dissolved in 1 ml of benzene. To the solution was added 0.45 ml of trimethyl phosphite, i.e. a compound (III) wherein $R^6$, $R^7$ and $R^8$ are all methyl. The mixture was refluxed with heating for 1 hour. The reaction mixture was cooled to room temperature and extracted with 10 ml of ethyl acetate. The extract was washed with a 5% aqueous solution of sodium hydroxide and then with a saturated aqueous solution of sodium chloride and dried over anhydrous sodium sulfate. The solvent was removed from the dried product at reduced pressure. The residue was separated and purified by silica gel column chromatography using a 1:1 benzene-ethyl acetate mixture as a developer. As a result, there was obtained 84.0 mg of a compound (Id) wherein R¹ is phenoxymethyl and R², $R^6$ and $R^7$ are all methyl. Yield 94%.

IR (CHCl₃, cm⁻¹) 1782, 1740, 1685.

NMR (CDCl₃, δ, ppm): 1.90 (s, 3H), 3.59 (s, 3H), 3.75 (s, 3H), 3.76 (s, 3H), 4.52 (s, 2H), 4.81 (s, 1H), 5.02 (s, 1H), 5.11 (s, 1H), 5.48–5.80 (m, 2H), 6.8–7.4 (5H), 7.67 (d, 1H).

EXAMPLES 26 TO 37

The procedure of Example 25 was repeated by using, as the starting material, compounds (II) wherein R¹ and R² are as defined in Table 2 given below and compounds (III) wherein $R^6$, $R^7$ and $R^8$ are as defined in Table 2, and employing the conditions as indicated in Table 3 given below. Thus compounds (Id) having the formula

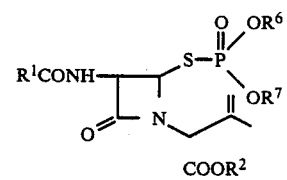

were prepared in the yields and with properties shown in Tables 3 to 5.

TABLE 2

| | Compound (II) | | | Compound (III) | | | |
|---|---|---|---|---|---|---|---|
| Example | R¹ | R² | Amount (mg) | R⁶ | R⁷ | R⁸ | Amount (ml) |
| 26 | PhOCH₂— | CH₃— | 100 | C₂H₅— | C₂H₅— | H | 0.27 |
| 27 | PhOCH₂— | PhCH₂— | 50 | C₂H₅— | C₂H₅— | H | 0.5 |
| 28 | PhOCH₂— | CCl₃CH₂— | 50 | C₂H₅— | C₂H₅— | H | 0.5 |
| 29 | PhOCH₂— | PhCH₂— | 50 | CH₃— | CH₃— | CH₃— | 0.5 |
| 30 | PhOCH₂— | PhCH₂— | 50 | Ph— | Ph— | H | 0.5 |
| 31 | PhOCH₂— | PhCH₂— | 50 | Ph— | Ph— | H | 0.2 |
| 32 | PhCH₂— | CH₃— | 55 | CH₃— | CH₃— | H | 0.5 |
| 33 | PhCH₂— | CH₃— | 50 | Ph— | Ph— | Ph— | 1.0 |
| 34 | PhCH₂— | CH₃— | 500 | C₂H₅— | C₂H₅— | H | 5 |
| 35 | PhCH₂— | PhCH₂— | 50 | C₂H₅— | C₂H₂— | H | 0.5 |
| 36 | PhCH₂— | PhCH₂— | 50 | CH₃— | CH₃— | CH₃— | 0.5 |
| 37 | PhCH₂— | PhCH₂— | 50 | Ph— | Ph— | H | 0.5 |

TABLE 3

| Example | Solvent | Temperature (°C.) | Time (hr) | Yield (%) |
|---|---|---|---|---|
| 26 | Benzene-acetonitrile (1 ml) (0.5 ml) | 18–20 | 18 | 83 |
| 27 | None | 60–62 | 4 | 93 |
| 28 | " | 58–61 | 3.5 | 97.5 |
| 29 | " | 50–55 | 10 | 85 |
| 30 | " | 50–53 | 3.5 | 85 |
| 31 | Tetrahydrofuran(0.5 ml) | 45–55 | 10 | 88 |
| 32 | None | 55–60 | 11.5 | 96 |
| 33 | " | 58–60 | 20 | 76 |
| 34 | " | 58–61 | 3.8 | 95 |
| 35 | " | 55–65 | 4 | 89 |
| 36 | " | 60–65 | 3 | 83 |
| 37 | " | 58–63 | 5 | 78 |

TABLE 4

| | Compound (Id) | | | |
|---|---|---|---|---|
| Example | R¹ | R² | R⁶ | R⁷ |
| 26 | PhOCH₂— | CH₃— | C₂H₅— | C₂H₅— |
| 27 | PhOCH₂— | PhCH₂— | C₂H₅— | C₂H₅— |
| 28 | PhOCH₂— | CCl₃CH₂— | C₂H₅— | C₂H₅— |
| 29 | PhOCH₂— | PhCH₂— | CH₃— | CH₃— |
| 30, 31 | PhOCH₂— | PhCH₂— | Ph— | Ph— |
| 32 | PhCH₂— | CH₃— | CH₃— | CH₃— |
| 33 | PhCH₂— | CH₃— | Ph— | Ph— |
| 34 | PhCH₂— | CH₃— | C₂H₅— | C₂H₅— |

TABLE 4-continued

| | Compound (Id) | | | |
|---|---|---|---|---|
| Example | $R^1$ | $R^2$ | $R^6$ | $R^7$ |
| 35 | PhCH$_2$— | PhCH$_2$— | C$_2$H$_5$— | C$_2$H$_5$— |
| 36 | PhCH$_2$— | PhCH$_2$— | CH$_3$— | CH$_3$— |
| 37 | PhCH$_2$— | PhCH$_2$— | Ph— | Ph— |

TABLE 5

| | IR | |
|---|---|---|
| Example | ($\nu$max, cm$^{-1}$) | $^1$H - NMR ( $\delta$, ppm) |
| 26 | 1780<br>1740<br>1685 | 1.31 (t, 6H), 1.94 (s, 3H),<br>3.82 (s, 3H), 3.9–4.4 (m, 4H),<br>4.60 (s, 2H), 4.91 (s, 1H),<br>5.10 (s, 1H), 5.23 (s, 1H),<br>5.4–6.0 (m, 2H), 6.9–7.6 (m, 5H),<br>7.95 (d, 2H) |
| 27 | 1783<br>1745<br>1690 | 1.25 (t, 6H), 1.87 (s, 3H),<br>3.7–4.4 (m, 4H), 4.53 (s, 2H),<br>4.81 (s, 1H), 5.02 (s, 1H),<br>5.10 (s, 1H), 5.15 (s, 2H),<br>5.4–5.8 (m, 2H), 6.7–7.5 (10H),<br>7.80 (d, 2H) |
| 28 | 1785<br>1748<br>1688 | 1.31 (t, 6H), 1.93 (s, 3H),<br>3.8–4.4 (m, 4H), 4.58 (s, 2H),<br>4.75 (s, 2H), 4.91 (s, 1H),<br>5.10 (s, 1H), 5.24 (s, 1H),<br>5.3–5.9 (m, 2H), 6.9–7.6 (m, 5H),<br>7.84 (d, 2H) |
| 29 | 1783<br>1745<br>1687 | 1.90 (s, 3H), 3.59 (s, 3H),<br>3.76 (s, 3H), 4.52 (s, 2H),<br>4.81 (s, 1H), 5.02 (s, 1H),<br>5.11 (s, 1H), 5.18 (s, 2H),<br>5.48–5.8 (m, 2H), 6.8–7.4 (10H),<br>7.67 (d, 1H) |
| 30, 31 | 1785<br>1747<br>1690 | 1.93 (s, 1H), 4.52 (s, 2H),<br>4.81 (s, 1H), 5.02 (s, 1H),<br>5.10 (s, 1H), 5.11 (s, 1H),<br>5.20 (s, 2H), 5.4–5.9 (m, 2H),<br>6.8–7.5 (10H), 7.60 (d, 1H) |
| 32 | 1780<br>1745<br>1673 | 1.89 (s, 3H), 3.59 (s, 3H),<br>3.63 (s, 2H), 3.70 (s, 3H),<br>3.75 (s, 3H), 4.76 (s, 1H),<br>5.01 (s, 1H), 5.11 (s, 1H)<br>5.30–5.8 (m, 2H), 6.70 (d, 1H),<br>7.30 (s, 5H) |
| 33 | 1782<br>1740<br>1660 | 1.86 (s, 3H), 3.37 (s, 3H),<br>3.39 (s, 2H), 4.75 (s, 1H),<br>4.95 (s, 1H), 5.05 (s, 1H),<br>5.18 (s, 2H), 5.1–5.7 (m, 2H),<br>6.55 (d, 1H), 7.2 (bs, 15H) |
| 34 | 1780<br>1740<br>1673 | 1.29 (t, 6H), 1.87 (s, 3H),<br>3.63 (s, 2H), 3.74 (s, 3H),<br>3.8–4.3 (m, 4H), 4.76 (s, 1H),<br>5.0 (s, 1H), 5.11 (s, 1H),<br>5.26–5.75 (m, 2H), 6.70 (d, 1H),<br>7.26 (s, 5H) |
| 35 | 1780<br>1740<br>1670 | 1.24 (t, 6H), 1.86 (s, 3H),<br>3.58 (s, 2H), 3.7–4.3 (m, 4H),<br>4.84 (s, 1H), 4.98 (s, 1H),<br>5.08 (s, 1H), 5.18 (s, 2H),<br>5.3–5.8 (m, 2H), 7–7.5 (10H),<br>7.72 (d, 1H) |
| 36 | 1780<br>1740<br>1665 | 1.86 (s, 3H), 3.57 (s, 2H),<br>3.60 (s, 3H), 3.76 (s, 3H),<br>4.84 (s, 1H), 4.95 (s, 1H),<br>5.07 (s, 1H), 5.18 (s, 2H),<br>5.3–5.9 (m, 2H), 6.9–7.5 (11H) |
| 37 | 1787<br>1745<br>1660 | 1.86 (s, 3H), 3.39 (s, 2H),<br>4.75 (s, 1H), 4.95 (s, 1H),<br>5.05 (s, 1H), 5.15 (s, 2H),<br>5.1–5.9 (m, 2H), 6.55 (d, 1H),<br>7.2 (bs, 20H) |

EXAMPLE 38

The procedure of Example 25 was followed replacing the starting material with a compound (II) wherein $R^1$ is p-methoxybenzyl and $R^2$ is p-chlorobenzyl and a compound (III) wherein $R^6$ is methyl, $R^7$ is methyl when $R^8$ is phenyl or $R^7$ is phenyl when $R^8$ is methyl. As a result, there were prepared two types of compounds (Id) at the same time, namely the compound (Id) [Compound (A)] wherein $R^1$ is p-methoxybenzyl, $R^2$ is p-chlorobenzyl, $R^6$ is methyl and $R^7$ is phenyl in a yield of 54% and the compound (Id) [Compound (B)] wherein $R^1$ is p-methoxybenzyl, $R^2$ is p-chlorobenzyl, $R^6$ and $R^7$ are both methyl in a yield of 32%. Compounds (A) and (B) were identified by IR and NMR.

| | Elementary analysis | | |
|---|---|---|---|
| | C | H | N |
| | Compound (A) | | |
| Calcd. (%): | 56.49 | 4.89 | 4.25 |
| Found (%): | 56.52 | 4.88 | 4.22 |
| | Compound (B) | | |
| Calcd. (%): | 52.30 | 5.07 | 4.69 |
| Found (%): | 52.28 | 5.05 | 4.73 |

EXAMPLE 39

The procedure of Example 25 was repeated by using a compound (II) wherein $R^1$ is phenoxymethyl and $R^2$ is p-nitrobenzyl and a compound (III) wherein $R^6$, $R^7$ and $R^8$ are all methyl. As a result, there was prepared a compound (Id) wherein $R^1$ is phenoxymethyl, $R^2$ is p-nitrobenzyl and $R^6$ and $R^7$ are both methyl. Yield 86%. The compound (Id) was identified by IR and NMR.

| | Elementary analysis | | |
|---|---|---|---|
| | C | H | N |
| Calcd. (%): | 50.59 | 4.75 | 7.08 |
| Found (%): | 50.62 | 4.76 | 7.11 |

EXAMPLE 40

The procedure of Example 25 was followed by using a compound (II) wherein $R^1$ is benzyl and $R^2$ is diphenylmethyl and a compound (III) wherein $R^6$, $R^7$ and $R^8$ are all phenyl, giving a compound (Id) wherein $R^1$ is benzyl and $R^2$ is diphenylmethyl and $R^6$ and $R^7$ are both phenyl. Yield 84%. The compound (Id) was identified by IR and NMR.

| | Elementary analysis | | |
|---|---|---|---|
| | C | H | N |
| Calcd. (%): | 67.19 | 5.10 | 3.82 |
| Found (%): | 67.16 | 5.10 | 3.83 |

EXAMPLE 41

A compound (Id) wherein $R^1$ is benzyl, $R^2$ is tert-butyl and $R^6$ and $R^7$ are both methyl was prepared by repeating the procedure of Example 25 using a compound (II) wherein $R^1$ is benzyl and $R^2$ is tert-butyl and a compound (III) wherein $R^6$ and $R^7$ are both methyl and $R^8$ is phenyl. Yield 89.5%. The compound was identified by IR and NMR.

| Elementary analysis | | | |
|---|---|---|---|
| | C | H | N |
| Calcd. (%): | 52.99 | 6.28 | 5.62 |
| Found (%): | 52.95 | 6.30 | 5.65 |

EXAMPLE 42

Into a reactor were placed 500 mg of a compound (Ia) wherein $R^1$ is benzyl, $R^2$ is methyl, $R^3$ is

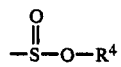

and $R^4$ is methyl, 50 ml of methylene chloride, 10.0 g of sodium chloride, 30 ml of water and 0.8 ml of acetic acid. The mixture was stirred to obtain a solution comprising two liquid phases. Electrolysis was continued at a temperature of 15° to 17° C. and a cathode current density of 10 mA/cm² by using platinum electrodes (1.5×2 cm²) and passing an electric charge of 3 F per mole of the starting material while stirring the mixture for 40 minutes. After the completion of the electrolysis, the organic phase was separated and washed with a saturated aqueous solution of sodium hydrogencarbonate and then with that of sodium chloride. The resulting product was dried over anhydrous sodium sulfate. The organic solvent was removed at reduced pressure. The residue was purified by silica gel column chromatography with use of a 5:1 benzene-ethyl acetate mixture as a developer, affording 445 mg of a compound (Ib) wherein $R^1$ is benzyl, $R^2$ is methyl, $R^3$ is

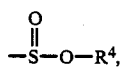

$R^4$ is methyl and X is Cl. Yield 82%.

IR ($\nu$max, cm$^{-1}$): 2970, 1780, 1760, 1675, 1540.

NMR (CDCl$_3$, δ, ppm): 3.40 (s, 3H), 3.54 (s, 2H), 3.71 (s, 3H), 4.20 (s, 2H), 4.46 (d, 1H), 4.82 (s, 1H), 4.95 (s, 1H), 5.33 (s, 1H), 5.52 (s, 1H), 6.42 (d, 1H), 7.23 (s, 5H).

EXAMPLES 43 TO 52

The procedure of Example 42 was repeated by using compounds (Ic) wherein $R^1$ and $R^2$ are as shown in Table 6 each in an amount of 50 mg and employing the conditions indicated in Tables 6 and 7. As a result, there were obtained compounds (Ib) represented by the formula

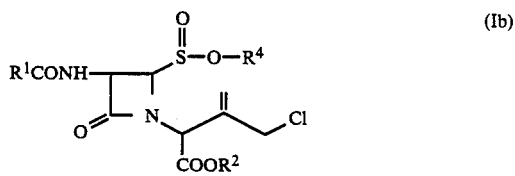

wherein $R^1$, $R^2$ and $R^4$ are as indicated in Table 8 and having the properties listed in Tables 8 and 9.

TABLE 6

| | Compound (Ic) | | | Water - Organic solvent | |
|---|---|---|---|---|---|
| Example | $R^1$ | $R^2$ | $R^4$ | (ml) | (ml) |
| 43 | PhCH$_2$— | CH$_3$— | CH$_3$— | 5 - methyl acetate | 5 |
| 44 | PhCH$_2$— | PhCH$_2$— | CH$_3$— | 3 - methylene chloride | 5 |
| 45 | PhCH$_2$— | PhCH$_2$— | CH$_3$— | 3 - methylene chloride | 5 |
| 46 | PhCH$_2$— | CCl$_3$CH$_2$— | CH$_3$— | 3 - 1,2-dichloroethane | 5 |
| 47 | PhCH$_2$— | CH$_3$— | C$_2$H$_5$— | 3 - chlorobenzene | 5 |
| 48 | PhOCH$_2$— | CH$_3$— | CH$_3$— | 3 - methylene chloride | 5 |
| 49 | PhOCH$_2$— | PhCH$_2$— | CH$_3$— | 3 - chloroform | 5 |
| 50 | PhOCH$_2$— | CCl$_3$CH$_2$— | CH$_3$— | 3 - methylene chloride | 5 |
| 51 | PhOCH$_2$— | p-NO$_2$—PhCH$_2$— | CH$_3$— | 3 - methylene chloride | 5 |
| 52 | PhOCH$_2$— | p-CH$_3$O—PhCH$_2$— | CH$_3$— | 3 - methylene chloride | 5 |

TABLE 7

| Example | Hydrochloric acid or chloride (g) | | Mineral acid or organic acid (ml) | | Electrode (1) | Amount (F/mol) (2) | Temperature (°C.) | Yield (%) (3) |
|---|---|---|---|---|---|---|---|---|
| 43 | NaCl | 1 | Sulfuric acid | 0.05 | Pt | 5 | 18–20 | 89 |
| 44 | NaCl | 1 | Acetic acid | 0.08 | C | 5 | 10–15 | 83.5 |
| 45 | MgCl$_2$ | 1 | Acetic acid | 0.08 | Pt | 5 | 16–18 | 81.8 |
| 46 | NaCl | 1 | Acetic acid | 0.08 | Pt | 3 | 18–21 | 83.5 |
| 47 | KCl | 1 | Sulfuric acid | 0.05 | Pt | 5 | 5–10 | 88.2 |
| 48 | NaCl | 1 | Sodium hydrogensulfate | 0.05 g | Pt | 5 | 20–23 | 82.5 |
| 49 | 35% HCl | 0.2 ml | — | | Pt | 5 | 20–21 | 82.0 |
| 50 | NaCl | 1 | Sulfuric acid | 0.05 | Pt | 5 | 18–21 | 88.0 |
| 51 | NaCl | 1 | Formic acid | 0.08 | Pt | 5 | 10–12 | 81.5 |
| 52 | NaCl | 1 | Acetic acid | 0.08 | Pt | 5 | 10–12 | 82.0 |

Note:
(1) Pt: Platinum electrode (1.5 × 2 cm²), C: Carbon electrode (1.5 × 2 cm²)
(2) Amount of electric charge (faraday) per mole of the compound (Ic)
(3) Yield of the compound (Ib) resulting from the purification by column chromatography.

TABLE 8

| Example | R¹ | R² | R⁴ | IR ($\nu$C=O, cm⁻¹) |
|---|---|---|---|---|
| 43 | PhCH₂— | CH₃— | CH₃— | Same as in Ex. 42 |
| 44 | PhCH₂— | PhCH₂— | CH₃— | 1782, 1762, 1665 |
| 45 | PhCH₂— | PhCH₂— | CH₃— | Same as in Ex. 44 |
| 46 | PhCH₂— | CCl₃CH₂— | CH₃— | 1785, 1758, 1675 |
| 47 | PhCH₂— | CH₃— | C₂H₅— | 1783, 1755, 1670 |
| 48 | PhOCH₂— | CH₃— | CH₃— | 1785, 1760, 1683 |
| 49 | PhOCH₂— | PhCH₂— | CH₃— | 1780, 1755, 1685 |
| 50 | PhOCH₂— | CCl₃CH₂— | CH₃— | 1780, 1760, 1690 |
| 51 | PhOCH₂— | p-NO₂—PhCH₂— | CH₃— | 1785, 1755, 1685 |
| 52 | PhOCH2 | p-CH₃O—PhCH₂— | CH₃— | 1785, 1760, 1690 |

TABLE 9

| Example | ¹H—NMR (δ, ppm) |
|---|---|
| 43 | Same as in Example 42 |
| 44 | 3.42 (s, 3H), 3.55 (s, 2H), 4.25 (s, 2H), 4.45 (d, 1H), 4.82 (s, 1H), 4.95 (s, 1H), 5.12 (s, 2H), 5.52 (s, 1H), 6.42 (d, 1H), 6.8–7.45 (10H) |
| 45 | Same as in Example 44 |
| 46 | 3.43 (s, 3H), 3.54 (s, 2H), 4.30 (s, 2H), 4.47 (d, 1H), 4.75 (s, 2H), 4.82 (s, 1H), 4.95 (s, 1H), 5.50 (s, 1H), 6.50 (d, 1H), 7.30 (s, 5H) |
| 47 | 3.50 (s, 2H), 3.75 (s, 3H), 4.18 (s, 2H), 4.48 (d, 1H), 4.85 (s, 1H), 4.70 (s, 1H), 5.43 (s, 1H), 5.60 (s, 1H), 6.7–7.4 (6H) |
| 48 | 3.38 (s, 3H), 3.69 (s, 3H), 4.20 (s, 2H), 4.42 (d, 1H), 4.52 (s, 2H), 4.82 (s, 1H), 4.95 (s, 1H), 5.33 (s, 1H), 5.50 (s, 1H), 6.5–7.5 (6H) |
| 49 | 3.40 (s, 3H), 4.25 (s, 2H), 4.50 (d, 1H), 4.55 (s, 2H), 4.85 (s, 1H), 4.90 (s, 1H), 5.12 (s, 2H), 5.35 (s, 1H), 5.55 (s, 1H), 6.5–7.5 (11H) |
| 50 | 3.41 (s, 3H), 4.23 (s, 2H), 4.47 (d, 1H), 4.52 (s, 2H), 4.75 (s, 2H), 4.82 (s, 1H), 4.97 (s, 1H), 5.36 (s, 1H), 5.53 (s, 1H), 6.45–7.5 (6H) |
| 51 | 3.40 (s, 3H), 4.22 (s, 2H), 4.45 (d, 1H), 4.53 (s, 2H), 4.82 (s, 1H), 4.98 (s, 1H), 5.20 (s, 2H), 5.33 (s, 1H), 5.52 (s, 1H), 6.45 (d, 1H), 6.6–8.3 (9H) |
| 52 | 3.41 (s, 3H), 3.87 (s, 3H), 4.20 (s, 2H), 4.42 (d, 1H), 4.52 (s, 2H), 4.82 (s, 1H), 4.95 (s, 1H), 5.18 (s, 2H), 5.33 (s, 1H), 5.52 (s, 1H), 6.5–7.5 (10H) |

EXAMPLE 53

In 3 ml of methylene chloride was dissolved 50 mg of a compound (Ia) wherein R¹ phenoxymethyl, R² is 2,2,2-trichloroethyl, R³ is

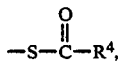

and R⁴ is methyl. To the solution were added 5 ml of a saturated aqueous solution of sodium chloride and 0.07 ml of sulfuric acid. The mixture was stirred to obtain a solution comprising two liquid phases. Electrolysis was continued for 20 minutes with stirring at a temperature of 18° to 20° C. and a cathode current density of 10 mA/cm² by using platinum electrodes (1.5×2 cm²). After the completion of the reaction, the methylene chloride was separated from the reaction mixture. Then the aqueous phase was extracted with methylene chloride. The extract was washed with a saturated aqueous solution of sodium chloride and dried over anhydrous sodium sulfate. The solvent was removed at reduced pressure. The residue was purified by silica gel column chromatography using a 5:1 benzene-acetic acid mixture as a developer, giving 48.4 mg of a compound (Ib) wherein R¹ is phenoxymethyl, R² is 2,2,2-trichloroethyl, R³ is

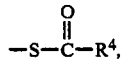

R⁴ is methyl and X is Cl. Yield 90.8%.

IR (CHCl₃, $\nu$max, cm⁻¹): 3370, 1780, 1750, 1695.

¹H-NMR (CDCl₃, δ, ppm): 2.08 (s, 3H), 4.17 (s, 2H), 4.49 (s, 2H), 4.78 (s, 1H), 4.80 (s, 2H), 5.05 (s, 2H), 5.42 (q, 1H), 5.96 (d, 1H), 6.6–7.4 (m, 5H), 7.65 (d, 1H).

EXAMPLE 54

Into a reactor were placed 30.5 mg of a compound (Ia) wherein R¹ is phenoxymethyl, R² is methyl, R³ is

and R⁵ is phenyl, 1.0 g of NaCl, 3 ml of water, 5 ml of methylene chloride and 0.07 ml of conc. sulfuric acid. The mixture was stirred to obtain a solution comprising two liquid phases. Electrolysis was continued for 15 minutes by use of platinum electrodes while passing an electric charge of 5 F/mol. After the completion of the reaction, the subsequent procedure of Example 42 was repeated to prepare 22.9 mg of a compound (Ib) wherein R¹ is phenoxymethyl, R² is methyl, R³ is

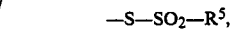

R⁵ is phenyl and X is Cl. Yield 92.4%.

IR (cm⁻¹): 3060, 2960, 1780, 1740, 1655, 1600, 1595, 1520, 1490, 1440, 1322, 1235, 1135, 1070.

NMR (CDCl₃, δ, ppm): 3.72 (s, 3H), 4.10 (s, 2H), 4.40 (s, 2H), 4.82 (s, 1H), 5.12 (s, 1H), 5.26 (s, 1H), 5.1–5.35 (m, 1H), 5.94 (d, J=6.6 Hz), 6.7–8.0 (m, 11H).

EXAMPLE 55

Into a reactor were placed 39.7 mg of a compound (Ia) wherein R¹ is benzyl, R² is methyl and R³ is

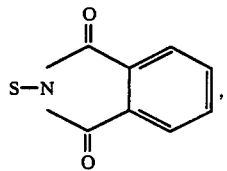

3 ml of methylene chloride and 15 ml of a saturated aqueous solution of sodium chloride. Then the mixture was stirred to obtain a solution comprising two liquid phases. Electrolysis was continued for 2 hours at a temperature of 19° C. and a cathode current density of 13 mA/cm² by using platinum electrodes while passing an electric charge of 32 F/mol. After the completion of the reaction, the subsequent procedure of Example 42 was repeated, giving 38.2 mg of a compound (Ib) as a colorless oily product wherein R¹ is benzyl, R² is methyl, R³ is

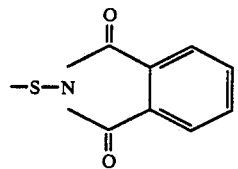

and X is Cl. Yield 89.5%.

NMR (CDCl₃, δ, ppm): 2.83 (s, 4H), 3.72 (s, 2H), 3.77 (s, 3H), 4.25 (s, 2H), 5.05 (s, 1H), 5.14 (d, 1H), 5.27 (dd, 1H), 5.40 (s, 1H), 5.59 (s, 1H), 7.0–7.5 (m, 6H).

EXAMPLE 56

Into a reactor were placed 34.65 mg of a compound (Ia) wherein R¹ is phenoxymethyl, R² is methyl, R³ is

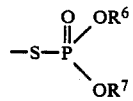

and, R⁶ and R⁷ are both ethyl, 4.5 g of magnesium chloride (6H₂O), 3 ml of water, 3 ml of ethyl acetate and 0.07 ml of conc. sulfuric acid. The mixture was stirred to obtain a solution comprising two liquid phases. Electrolysis was continued for 30 minutes with stirring at a temperature of 18° to 20° C. and a cathode current density of 30 mA/cm² by using platinum electrodes while passing an electric charge of 8 F/mol. After the completion of the reaction, the subsequent procedure of Example 42 was effected, giving 34.34 mg of a compound (Ib) wherein R¹ is phenoxymethyl, R² is methyl, R³ is

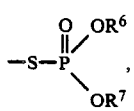

R⁶ and R⁷ are both ethyl and X is Cl. Yield 92.8%.

IR (cm⁻¹): 2980, 2960, 2940, 1780, 1745, 1690, 1603, 1580, 1495, 1440, 1250, 1010, 810, 740, 720.

NMR (CDCl₃, δ, ppm): 1.31 (dt, 6H), 3.78 (s, 3H), 4.09 (m, 4H), 4.20 (s, 2H), 4.50 (s, 2H), 5.10 (s, 1H), 5.21 (s, 1H), 5.55 (s, 1H), 5.2–5.85 (m, 2H), 6.7–7.4 (m, 5H), 7.6 (d, J=10.5 Hz, 1H).

EXAMPLE 57

The procedure of Example 42 was repeated by using a compound (Ia) wherein R¹ is p-chlorobenzyl, R² is p-nitrobenzyl, R³ is

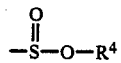

and R⁴ is isopropyl. Thereby there was obtained a compound (Ib) wherein R¹ is p-chlorobenzyl, R² is p-nitrobenzyl, R³ is

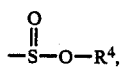

R⁴ is isopropyl and X is Cl in a yield of 84%. The compound was identified by IR and NMR.

| | Elementary analysis | | |
|---|---|---|---|
| | C | H | N |
| Calcd. (%): | 50.98 | 4.45 | 6.86 |
| Found (%): | 50.61 | 4.44 | 6.85 |

EXAMPLE 58

The procedure of Example 42 was repeated by using a compound (Ia) wherein R¹ is p-nitrophenoxymethyl, R² is phenoxymethyl, R³ is

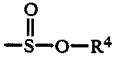

and R⁴ is tert-butyl. As a result, there was obtained a compound (Ib) wherein R¹ is p-nitrophenoxymethyl, R² is phenoxymethyl, R³ is

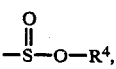

R⁴ is n-butyl and X is Cl. Yield 82.0%. The compound was identified by IR and NMR.

| | Elementary analysis | | |
|---|---|---|---|
| | C | H | N |
| Calcd. (%): | 51.96 | 4.85 | 6.73 |
| Found (%): | 51.92 | 4.84 | 6.75 |

EXAMPLE 59

The procedure of Example 53 was repeated by using a compound (Ia) wherein R¹ is p-methoxybenzyl, R² is 2-chloroethyl, R³ is

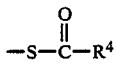

and $R^4$ is ethyl. As a result, there was produced a compound (Ib) wherein $R^1$ is p-methoxybenzyl, $R^2$ is 2-chloroethyl, $R^3$ is

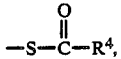

$R^4$ is ethyl and X is Cl. Yield 87.0%. The compound was identified by IR and NMR.

| | Elementary analysis | | |
|---|---|---|---|
| | C | H | N |
| Calcd. (%): | 51.06 | 5.07 | 5.41 |
| Found (%): | 51.08 | 5.06 | 5.37 |

EXAMPLE 60

The procedure of Example 53 was repeated by using a compound (Ia) wherein $R^1$ is p-methoxyphenoxymethyl, $R^2$ is diphenylmethyl, $R^3$ is

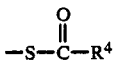

and $R^4$ is n-propyl. As a result, there was obtained a compound (Ib) wherein $R^1$ is p-methoxyphenoxymethyl, $R^2$ is diphenylmethyl, $R^3$ is

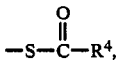

$R^4$ is n-propyl and X is Cl. Yield 85.5%. The compound was identified by IR and NMR.

| | Elementary analysis | | |
|---|---|---|---|
| | C | H | N |
| Calcd. (%): | 62.70 | 5.43 | 4.30 |
| Found (%): | 62.73 | 5.40 | 4.29 |

EXAMPLE 61

The procedure of Example 54 was repeated by using a compound (Ia) wherein $R^1$ is benzyl, $R^2$ is p-nitrophenoxymethyl, $R^3$ is

and $R^5$ is phenyl, giving a compound (Ib) wherein $R^1$ is benzyl, $R^2$ is p-nitrophenoxymethyl, $R^3$ is

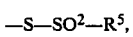

$R^5$ is phenyl and X is Cl. Yeild 83%. The compound was identified by IR and NMR.

| | Elementary analysis | | |
|---|---|---|---|
| | C | H | N |
| Calcd. (%): | 52.76 | 3.98 | 6.37 |
| Found (%): | 52.79 | 3.97 | 6.38 |

EXAMPLE 62

A compound (Ib) wherein $R^1$ is phenoxymethyl, $R^2$ is p-methoxybenzyl, $R^3$ is

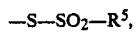

$R^5$ is p-chlorophenyl and X is Cl was prepared by the same process as in Example 54 with the exception of using a compound (Ia) wherein $R^1$, $R^2$, $R^3$ and $R^5$ are as defined above. Yield 86.5%. The compound (Ib) was identified by IR and NMR.

| | Elementary analysis | | |
|---|---|---|---|
| | C | H | N |
| Calcd. (%): | 53.01 | 4.16 | 4.12 |
| Found (%): | 53.04 | 4.15 | 4.15 |

EXAMPLE 63

A compound (Ib) wherein $R^1$ is p-nitrobenzyl, $R^2$ is phenoxymethyl, $R^3$ is

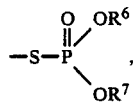

$R^6$ and $R^7$ are both n-propyl and X is Cl was prepared in the same manner as in Example 56 with the exception of using a compound (Ia) wherein $R^1$, $R^2$, $R^3$, $R^6$ and $R^7$ are defined above. Yield 83%.

| | Elementary analysis | | |
|---|---|---|---|
| | C | H | N |
| Calcd. (%): | 50.91 | 5.17 | 6.14 |
| Found (%): | 50.94 | 5.14 | 6.15 |

EXAMPLE 64

A compound (Ib) wherein $R^1$ is phenoxymethyl, $R^2$ is benzyl, $R^3$ is

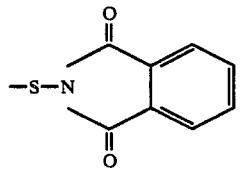

and X is Cl was prepared in the same manner as in Example 55 with the exception of using a compound (Ia) wherein $R^1$, $R^2$ and $R^3$ are as defined above. Yield 83.5%. The compound was identified by IR and NMR.

|  | Elementary analysis | | |
|---|---|---|---|
|  | C | H | N |
| Calcd. (%): | 60.04 | 4.23 | 6.78 |
| Found (%): | 60.01 | 4.22 | 6.81 |

EXAMPLE 65

Synthesis of the ester of 3-chloromethyl-7-phenylacetamide-3-cephem-4-carboxylic acid and benzyl alcohol having the formula

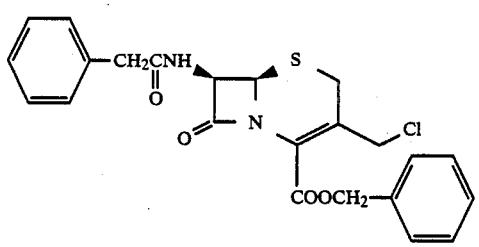

Into a reactor were placed 101 mg of the ester of 3-chloromethyl-2-(3-phenylacetamide-4-phenylsulfonylthio-2-azetidinone-1-yl)-3-butenoic acid and benzyl alcohol having the formula

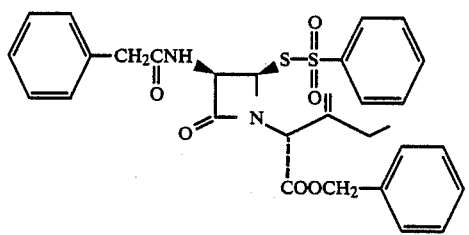

and 1 ml of dried dimethylformamide (DMF). The contents of the reactor were mixed together to obtain a uniform solvent. The reactor was cooled to $-25°$ C. by being placed into a Dry Ice-acetone bath. 28% ammonia water (15.5 μl) was added and the mixture was stirred for 1 hour while maintaining the temperature at $-30°$ to $-20°$ C. After the completion of the reaction, thereto were added 5 drops of 5% hydrochloric acid and then about 30 ml of ethyl acetate. The reaction mixture was poured into an aqueous solution of sodium chloride with ice floating thereon, thereby separating the organic phase. The organic phase thus obtained was washed twice with a saturated aqueous solution of sodium chloride, dried over anhydrous sodium sulfate and concentrated. The residue was purified by silica gel column chromatography, giving 68 mg of the ester of 3-chloromethyl-7-phenylacetamide-3-cephem-4-carboxylic acid and benzyl alcohol. Yield 88%. The compound was identified by IR and NMR.

IR (CHCl$_3$, cm$^{-1}$): 1790, 1730, 1682.

NMR (CDCl$_3$, δ, ppm): 3.32 and 3.60 (2H, ABq, 18 Hz), 3.53 (2H, s), 4.31 and 4.45 (2H, ABq, 12 Hz), 4.86 (1H, d, 5 Hz), 5.20 (2H, s), 5.77 (1H, d.d, 5 Hz, 9.2 Hz), 6.43 (1H, d, 9.2 Hz), 7.27 (5H, s), 7.33 (5H, s).

EXAMPLE 66

Preparation of the ester of 3-chloromethyl-7-phenylacetamide-3-cephem-4-carboxylic acid and benzyl alcohol.

Into a reactor were placed 34 mg of the ester of 3-chloromethyl-2-(3-phenylacetamide-4-phenylsulfonylthio-2-azetidinone-1-yl)-3-butenoic acid and benzyl alcohol and 0.4 ml of dried DMF, followed by mixing of the contents to obtain a uniform solvent. The reactor was cooled to $-35°$ C. by being placed into a Dry Ice-acetone bath. Subsequently into the reactor was charged 0.125 ml of the DMF prepared by forcing ammonia gas thereinto to a ammonia concentration of 11.4 mg/ml. The resulting mixture was stirred for 1 hour while being maintained at $-40°$ to $-35°$ C. After the completion of the reaction, the reaction mixture was subjected to the same treatment as in Example 65. As a result, there was obtained 18.8 mg of the ester of 3-chloromethyl-7-phenylacetamide-3-cephem-4-carboxylic acid and benzyl alcohol. Yield 74%.

The compound thus obtained was analyzed with the results identical with those obtained in Example 65.

EXAMPLES 67 TO 76

The procedure of Example 65 was repeated by using the azetidinone derivatives (Ib) having the formula

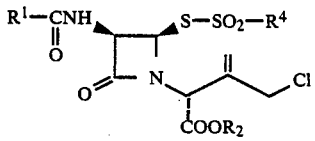

wherein R$^1$, R$^2$ and R$^4$ are as shown in Table 10 and employing the reaction conditions as indicated in Table 10. As a result, there were obtained derivatives of 3-chloromethyl-3-cephem(IV) having the formula

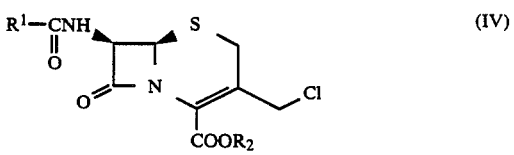

(IV)

and shown in Table 11 as having the properties set forth therein.

TABLE 10

| Example | Derivative (Ib) | | | | Ammonia | | | | |
|---|---|---|---|---|---|---|---|---|---|
| | R$^1$ | R$^2$ | R$^4$ | Amount (mg) | DMF (ml) | water (μl) | Temp. (°C.) | Time (hr) | Yield (%) |
| 67 | PhCH$_2$— | CH$_3$— | Ph | 100 | 0.5 | 36 | −30/−20 | 1 | 72 |
| 68 | PhCH$_2$— | CH$_3$— | p-CH$_3$—Ph- | 48 | 0.5 | 16.5 | −30/−20 | 1 | 59 |
| 69 | PhCH$_2$— | CH$_3$— | p-Cl—Ph- | 53 | 0.5 | 17.5 | −30/−20 | 1 | 70 |
| 70 | PhCH$_2$— | CH$_3$— | p-NO$_2$—Ph- | 45 | 0.5 | 7.5 | −30/−20 | 1 | 84 |
| 71 | PhCH$_2$— | CH$_3$— | o-NO$_2$—Ph- | 48 | 0.5 | 15.5 | −30/−20 | 1 | 44 |

TABLE 10-continued

| | Derivative (Ib) | | | Amount | DMF | Ammonia water | Temp. | Time | Yield |
|---|---|---|---|---|---|---|---|---|---|
| Example | $R^1$ | $R^2$ | $R^4$ | (mg) | (ml) | ($\mu$l) | (°C.) | (hr) | (%) |
| 72 | $PhCH_2-$ | $PhCH_2-$ | p-$CH_3O$—Ph- | 45 | 0.5 | 13 | −30/−20 | 1 | 72 |
| 73 | $PhCH_2-$ | $PhCH_2-$ | p-$NO_2$—Ph- | 43 | 0.5 | 6.1 | −40/−35 | 1 | 70 |
| 74 | $PhCH_2-$ | $-CH_2CCl_3$ | p-$NO_2$—Ph- | 47 | 0.5 | 12.6 | −30/−20 | 1 | 51 |
| 75 | $PhCH_2$ | p-$NO_2$—$PhCH_2-$ | p-$NO_2$—Ph- | 56 | 0.5 | 15 | −30/−20 | 1 | 67 |
| 76 | $PhOCH_2-$ | $PhCH_2$ | p-$NO_2$—Ph | 60 | 0.5 | 16.5 | −30/−20 | 1 | 83 |

TABLE 11

| Example | $R^1$ | $R^2$ | IR ($CHCl_3$, $cm^{-1}$) | NMR ($CDCl_3$) |
|---|---|---|---|---|
| 67, 68, 69, 70, 71 | $PhCH_2-$ | $CH_3$ | 1787<br>1730<br>1680 | 3.38 and 3.60 (2H, ABq, 18Hz),<br>3.60 (2H, s), 3.83 (3H, s),<br>4.40 and 4.57 (2H, ABq, 12Hz),<br>4.95 (1H, d, 5Hz),<br>5.78 (1H, d.d, 5Hz, 9.2Hz),<br>6.18 (1H, d, 9.2Hz), 7.27 (5H, s) |
| 72, 73 | $PhCH_2-$ | $PhCH_2-$ | Identical with the values obtained in Example 65 | |
| 74 | $PhCH_2-$ | $CH_2CCl_3$ | 1797<br>1725<br>1680 | 3.50 and 3.67 (2H, ABq, 18Hz)<br>3.65 (2H, s), 4.51 (2H, s),<br>4.80 and 4.97 (2H, ABq, 12Hz),<br>5.03 (1H, d, 5Hz),<br>5.88 (1H, d.d, 5Hz, 9.2Hz),<br>6.28 (1H, d, 9.2Hz), 7.30 (5H, s) |
| 75 | $PhCH_2-$ | p-$NO_2$—Ph- | 1790<br>1730<br>1695 | 3.45 and 3.63 (2H, ABq, 18Hz),<br>3.63 (2H, s),<br>4.41 and 4.57 (2H, ABq, 12Hz),<br>4.97 (1H, d, 5Hz), 5.37 (2H, s),<br>5.87 (1H, d.d, 5Hz, 9.2Hz),<br>6.3 (1H, d, 9.2Hz), 7.30 (5H, s),<br>7.55 (2H, d, 9Hz), 8.21 (2H, d, 9Hz) |
| 76 | $PhOCH_2-$ | $PhCH_2-$ | 1790<br>1730<br>1690 | 3.50 and 3.55 (2H, ABq, 18Hz),<br>4.40 and 4.53 (2H, ABq, 12Hz),<br>4.52 (2H, s), 4.97 (1H, d, 5Hz),<br>5.29 (2H, s),<br>5.73 (1H, d.d, 5Hz, 9.2Hz),<br>6.48 (1H, d, 9.2Hz), 7.32 (5H, s),<br>6.7–7.6 (5H, m) |

We claim:

1. A process for preparing an azetidinone derivative represented by the formula:

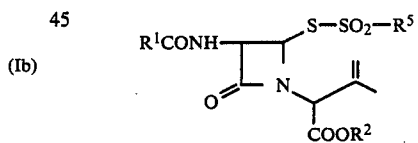

(Ib)

wherein
$R^1$ is lower alkyl mono-substituted with aryl or with aryloxy, the aryl being optionally substituted with hydroxy, methoxy, chloro or nitro and the aryloxy being optionally substituted with hydroxy, methoxy or nitro;
$R^2$ is lower alkyl mono- or di-substituted with aryl or with aryloxy, the aryl being optionally substituted with methoxy, chloro or nitro, and the aryloxy being optionally substituted with nitro, or $R^2$ is lower alkyl optionally mono- or tri-substituted with halogen;
$R^5$ is aryl optionally substituted with hydroxy, chloro, nitro, methyl or methoxy; and
$X'$ is a halogen, the process comprising subjecting to electrolysis an azetidinone derivative represented by the formula:

$$\text{R}^1\text{CONH}\begin{array}{c}\text{S}-\text{SO}_2-\text{R}^5\\ \diagup\\ \text{N}\\ \text{O} \quad \quad \text{COOR}^2\end{array}$$

wherein $R^1$, $R^2$ and $R^5$ are as defined above in the presence of at least one member selected from the group consisting of hydrohalogenic acid and halide.

2. A process according to claim 1 wherein the electrolysis is conducted by incorporating mineral acid or organic acid in the reaction system.

3. A process according to claim 1 wherein the electrolysis is conducted in an ester of lower carboxylic acid or hydrocarbon halide.

4. A process according to claim 1 wherein the electrolysis is conducted at a temperature of −30° to 60° C.

* * * * *